(12) United States Patent
Budach et al.

(10) Patent No.: US 9,243,224 B2
(45) Date of Patent: *Jan. 26, 2016

(54) CELL CULTURE MEDIUM

(71) Applicant: NOVARTIS AG, Basel (CH)

(72) Inventors: Wolfgang Ernst Gustav Budach, Basel (CH); Helene C. Chassin, Basel (CH); Kerstin Dorsch, Basel (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/620,359

(22) Filed: Feb. 12, 2015

(65) Prior Publication Data

US 2015/0218509 A1    Aug. 6, 2015

Related U.S. Application Data

(63) Continuation of application No. 13/695,002, filed as application No. PCT/EP2011/056509 on Apr. 25, 2011, now Pat. No. 8,986,957.

(60) Provisional application No. 61/327,837, filed on Apr. 26, 2010.

(51) Int. Cl.
| | |
|---|---|
| *C12N 5/00* | (2006.01) |
| *C12N 5/07* | (2010.01) |
| *C07K 16/00* | (2006.01) |

(52) U.S. Cl.
CPC ............... *C12N 5/005* (2013.01); *C07K 16/00* (2013.01); *C12N 5/0018* (2013.01); *C12N 5/0031* (2013.01); *C07K 2317/14* (2013.01); *C12N 2500/32* (2013.01); *C12N 2500/38* (2013.01); *C12N 2500/95* (2013.01); *C12N 2500/99* (2013.01); *C12N 2510/02* (2013.01)

(58) Field of Classification Search
None
See application file for complete search history.

(56) References Cited

U.S. PATENT DOCUMENTS

| 4,767,704 | A | 8/1988 | Cleveland et al. |
|---|---|---|---|
| 5,122,469 | A | 6/1992 | Tsao |
| 6,048,728 | A | 4/2000 | Inlow |
| 8,198,084 | B2 * | 6/2012 | Gorfien .................. C07K 14/61 |
| | | | 435/174 |
| 2006/0160180 | A1 | 7/2006 | Wang |
| 2006/0194323 | A1 | 8/2006 | Judd |
| 2009/0061516 | A1 | 3/2009 | Plavsic |
| 2011/0111495 | A1 | 5/2011 | Hao |

FOREIGN PATENT DOCUMENTS

| SU | 162294 A1 | 4/1964 |
|---|---|---|
| WO | 9215670 A1 | 9/1992 |
| WO | 9512664 A1 | 5/1995 |
| WO | 02101019 A2 | 12/2002 |
| WO | 2006050050 A2 | 5/2006 |
| WO | 2007003640 A1 | 1/2007 |
| WO | 2008141207 A1 | 11/2008 |
| WO | 2010036767 A1 | 4/2010 |

* cited by examiner

*Primary Examiner* — Suzanne M Noakes
*Assistant Examiner* — Jae W Lee
(74) *Attorney, Agent, or Firm* — James Lynch

(57) ABSTRACT

A cell culture medium with high content of choline chloride is provided. The cell culture media further comprise only moderate amounts of amino acids, in particular the amount of glutamine in the cell culture media is limited. The cell culture media can be used for large scale production of polypeptides using cell cultures. The cell culture media with high content of choline chloride are particularly suitable for fed-batch cell culture whereby cell viabilities stay at a higher level for a longer time and high polypeptide titers although limited amounts of amino acids are used.

7 Claims, 24 Drawing Sheets

CELL CULTURE MEDIUM

TECHNICAL FIELD OF THE INVENTION

This invention relates to the general field of biotechnology, particularly the cultivation of cells and their use for the production of polypeptides at industrial scale.

The present invention provides cell culture media with high content of choline chloride which allows cultivation of cells with high cell viabilities over a prolonged period of time. The cell culture media according to the present invention further allow obtaining high polypeptide productivities and/or improved product quality when used for the production of a polypeptide by recombinant expression of polypeptides using CHO cell culture systems, in particular at industrial scale.

TECHNICAL BACKGROUND OF THE INVENTION

The preparation of polypeptides using recombinant technology has developed into a standard procedure during the last couple of decades. The access to recombinant polypeptides by cloning the genes encoding the respective polypeptide followed by subsequent transformation of suitable expression hosts with the gene to be expressed and final production and purification of the obtained recombinant polypeptide product has provided access to a whole new class of biologically designed and produced therapeutics.

Pharmaceutically active compounds have been prepared in increasing numbers in the pharmaceutical industry using recombinant DNA technology followed by production processes developed in the field of bioengineering.

Such biological products include monoclonal antibodies, which have been developed into important treatment options in various medical fields including autoimmune diseases, inflammatory disorders, immunosuppression, oncology or the like.

Development of such therapeutics of biological origin requires production at industrial scale thereby providing access to large amounts of recombinant polypeptide. Preferred expression systems are mammalian cell cultures which are superior to most other eukaryotic systems based on insect cells, yeast or the like, or even traditional prokaryotic expression systems.

However, mammalian cell culture includes tremendous challenges especially at the industrial scale. Production facilities for mammalian cell culture require thorough optimization of many process conditions.

One of the most important process parameters for controlling the overall production process is the medium in which cells are grown. Suitable cell culture media must provide cell cultures with all necessary nutrients, which is especially difficult if no components of animal origin like serum or proteins, e.g. growth factors, are added to the media.

Further, mammalian cell cultures require particular supplement components at different stages of the polypeptide production process. Accordingly, cell culture media must provide the necessary substrates during a) initial growth and proliferation of the host cells at lower densities; b) subsequent cultivation of cells to high densities; c) the actual process of polypeptide formation in the cultured cells.

The overall process for the production of recombinant polypeptide preferably comprises an expansion phase and a production phase. During expansion phase the host cells are cultivated to high densities by using a growth medium in order to maximize subsequent polypeptide production later on. During production phase the actual formation of the desired polypeptide in large amounts is achieved by use of a production medium. In order to meet the specific metabolic requirements of the cells in each phase of the overall polypeptide production process, different media compositions have been designed for expansion and production phase respectively. For instance, production media often contain higher amounts of amino acids than growth media.

Accordingly, considerable efforts have been taken in the past to develop cell culture media with special emphasis on their use for large scale production of polypeptides. Nevertheless, continuous improvement of cell culture media is still an important goal in order to further maximize polypeptide production in terms of product quality and quantitative yields.

Many components of cell culture media have been investigated in the past in terms of their role for polypeptide production. Possible targets are inorganic salts, amino acids, sources of carbon like glucose, or vitamins.

For instance, it has been demonstrated that supplementation of compounds like vitamins, choline chloride or amino acids can increase viability and productivity of cells cultivated under protein-free conditions (Kim do Y et. al., Cytotechnology 2005, 47, 37-49).

Choline chloride is a standard component of cell culture media which served as a phospholipid precursor for the cells. After being taken up and being processed by the cells, it ends up, besides phosphatidylethanolamine and phosphatidylinositol as one of the major phospholipids in cell membranes called phosphatidyl choline.

Commonly used cell culture media like D-MEM (Dulbecco's Modified Eagle Medium) and D-MEM/F-12 have been widely used for the growth of a wide range of mammalian cell lines. These media include amounts of choline chloride of 4 mg/L and 8.98 mg/L, respectively.

Other commercially available media like Ham's F-12 (commercially available from BioConcept) and MEM (commercially available form HyClone) also comprise low amounts of choline chloride of 13.96 mg/L and 56 mg/L, respectively.

U.S. Pat. No. 6,180,401 discloses an improved method for producing a polypeptide in animal cell culture. One objective is to increase the final product concentration. Several parameters are modified in order to maximize product yield in the production phase including glucose concentration, osmolality and glutamine concentration. U.S. Pat. No. 6,180,401 discloses cell culture media, which have a content of choline chloride of 50.86 mg/L.

U.S. Pat. No. 5,122,469 discloses a culture medium for propagating various mammalian cell lines, in particular Chinese hamster ovary cells (CHO), and allows the cultivation of cells at high densities as monolayers or in suspension suitable for small and large scale propagation of mammalian cells. One further advantage is an enhanced yield of product. The medium is a chemically defined culture medium containing elevated levels of certain amino acids. The content of choline chloride is 50.86 mg/L.

Only very few media with high content of choline chloride are known in the prior art. Waymouth has described a cell culture medium, which can be used for the culture of the mouse L929 fibroblast connective tissue cell line (C. Waymouth, J. Natl. Cancer. Inst., 1959, 22, 1003-1017). This medium is a serum-free, chemically defined synthetic medium and has a content of choline chloride of 250 mg/L. This medium is commercially available under the name Waymouth's Medium MB 752/1 (BioConcept and Sigma-Aldrich). Known applicability is limited to whole organ culture, establishment of carcinoma cell lines from pleural effusions, and the growth of potentially tumorigenic cells prior to their assessment in vivo.

WO 02/101019 discloses two medium compositions with relatively high content of choline chloride, 101.72 mg/L and 209.40 mg/L, respectively. These media were used for studying the impact of glutamine and glutamate for recombinant protein production. However, both media still contained high amounts of glutamine.

Only limited information is available from the prior art as far as the role of the choline chloride content in cell culture media for polypeptide production is concerned. U.S. Pat. No. 6,048,728 briefly discusses the role of choline chloride content in cell culture media for the production of biological products using hybridoma cells. In the case of antibody expressing cells, secretion of maximum amounts of antibody was observed in media containing a choline supplement of greater than 4 mg/L and preferably of approximately 4 to 75 mg/L, in combination with the other reagents of the Primary Supplement. At these concentrations, choline is described to be not limiting and being without apparent toxicity.

Production cell culture media, especially those designed for use in industrial large scale production of recombinant polypeptides requires increased amounts of components, for instance amino acids.

However, highly concentrated cell culture media show limited solubility of selected media components. Limited solubility represents a technical disadvantage because highly concentrated media for large scale production bear the risk of precipitation of individual components, for instance during the production phase and especially during storage. This can lead to variations of the media composition and to a deterioration of the cell culture conditions at the critical point of product formation.

As a further consequence, precipitation leads to the effective removal of precious media components from the actual production process. Additional recycling processes designed for overcoming sued drawbacks are technically difficult to realize and require further effort in terms of resources and time. Less concentrated cell culture media, when equally effective in polypeptide production, would allow achieving significant cost reductions in industrial production processes.

Considering the above challenges and existing disadvantages, there is a continued need in the field of industrial biotechnology for improved culture media which allow producing recombinant polypeptides at an industrial scale with even higher yields, i.e. improved specific and overall productivity, and increased product quality. Improved cell culture media ere especially desirable for improvement of productivity during production phase.

A specific technical objective of polypeptide production processes is to maintain higher cell viabilities at the end of the production process in order to maximize the final yield of polypeptide, in particular due to prolongation of the production time. Moreover, reducing the aggregation of the formed recombinant polypeptide and improved product quality particularly in terms of posttranslational modifications, such as glycosylation pattern is also an important technical objective.

Finally, improved production media for large scale production of polypeptides are desirable which contain reduced amounts of components while being equally effective or even better in terms of cell growth, polypeptide productivity, recombinant polypeptide quality and polypeptide functionality.

SUMMARY OF THE INVENTION

In order to address the technical challenges referred to above, the present invention provides cell culture media with high content of choline chloride, which leads to an unexpected improvement of cell specific productivity and cell viability, especially at the later stages of biotechnological production processes. Further, the quality of the recombinant product by use of the cell culture media can also be surprisingly improved. The cell culture media according to the present invention are especially suitable for use during production phase. Accordingly, the present invention allows producing recombinant polypeptide from CHO cells.

The cell culture media can be used in particular as production medium in order to achieve high cell growth, high viable cell densities and high polypeptide titer during production phase, it is also be found that the product quality in terms of less aggregation and/or better posttranslational modification, such as improved glycosylation pattern of the recombinant product, can be improved by use of the cell culture media according to the present invention.

In the present invention, choline chloride is preferably used. However, other sources of choline, for instance choline hydroxide, choline tartrate/bitartrate, choline sulphate, choline phosphate or any other choline compound based on the use of a different counterion is also suitable for use in the cell culture media according to the present invention. If such other choline compounds are used, their amount is preferably chosen so as to achieve the same molar choline concentration as is achieved by using choline chloride in the concentration ranges and values given above, i.e. the other choline salt is preferably present in a concentration equivalent to the concentration of the choline chloride as outlined. This also holds true for the specific aspects and embodiments referred to below.

According to the first aspect of the present invention, a cell culture medium is provided with a content of choline chloride in the range of 60 mg/L to 2500 mg/L. The choline chloride content in the cell culture medium may be 80 mg/L or higher, alternatively 160 mg/L or higher, 200 mg/L or higher or 220 mg/L or higher. The content of the choline chloride in the cell culture medium is limited to 2500 mg/L, alternatively 1000 mg/L, 840 mg/L, 500 mg/L or 300 mg/L. Choline chloride may be present at a concentration of about 240 mg/L.

The cell culture medium according to the first aspect of the invention further comprises only a limited content of amino acids expressed by a total concentration of amino acids of from 20 to 57 mmol/L. Alternatively, the total amino acids concentration is above 25 mmol/L, above 30 mmol/L, above 35 mmol/L or even above 40 mmol/L. Further, the total amino acids concentration can be below 54 mmol/L. The total amino acids concentration can for instance be about 51 mmol/L.

Further, the cell culture medium optionally comprises a reduced content of glutamine. In particular, glutamine is present in a concentration of 500 to 1400 mg/L, alternatively 800 to 1400 mg/L, or even 900 to 1200 mg/L.

The content of amino acids in the cell culture medium according to the first aspect of the invention can optionally comprise the following amino acids in the following concentrations expressed in mmol/l:

| | |
|---|---|
| Arginine | 4.0-6.0, preferably 4.5-5.5 |
| Asparagine | 3.0-6.0, preferably 4.0-5.5 |
| Aspartic acid | 2.5-4.0, preferably 3.0-3.6 |
| Glycine | 0.3-0.8, preferably 0.5-0.7 |
| Histidine | 0.6-1.0, preferably 0.7-0.9 |
| Isoleucine | 2.0-5.0, preferably 3.0-4.0 |
| Leucine | 3.0-7.0, preferably 3.5-6.0 |
| Lysine | 2.0-4.0, preferably 2.5-3.5 |
| Methionine | 1.0-1.5, preferably 1.2-1.4 |
| Phenylalanine | 1.0-2.0, preferably 1.3-1.8 |

-continued

| | |
|---|---|
| Proline | 2.5-6.0, preferably 3.0-5.5 |
| Serine | 3.0-8.0, preferably 4.0-7.0 |
| Threonine | 2.0-3.5, preferably 2.5-3.1 |
| Tryptophane | 0.4-1.0, preferably 0.5-0.8 |
| Valine | 2.5-5.0, preferably 3.0-4.5 |
| Tyrosine | 1.0-2.0, preferably 1.2-1.8 |
| Cystine | 0.5-1.0, preferably 0.6-0.8 |

The cell culture media are preferably serum-free and protein-free. Preferably, they are also free of protein hydrolysates.

According to a second aspect of the present invention a process for the production of a recombinant polypeptide is provided comprising a production phase wherein recombinant CHO cells are cultured in the cell culture media according to the first aspect of the invention.

The recombinant polypeptide prepared is in particular a recombinant antibody.

In the process of the invention, the cells are preferably cultured in a fed-batch process.

BRIEF DESCRIPTION OF THE DRAWINGS

FIG. 1 depicts the normalized viable cell densities of cells expressing mAb1 cultivated in shake flasks as a function of time in three different cell culture media (Experiment 1).

FIG. 2 depicts the viability of cells expressing mAb1 cultivated in shake flasks as a function of time in three different cell culture media (Experiment 1).

FIG. 3 depicts the normalized polypeptide titer obtained after cultivation of cells expressing mAb1 in shake flasks as a function of time for three different media (Experiment 1).

FIG. 4 depicts the normalized viable cell densities of cells expressing mAb2 cultivated in shake flasks as a function of time in three different cell culture media (Experiment 2).

FIG. 5 depicts the viability of cells expressing mAb2 cultivated in shake flasks as a function of time in three different cell culture media (Experiment 2).

FIG. 6 depicts the normalized polypeptide titer obtained after cultivation of cells expressing mAb2 in shake flasks as a function of time for three different media (Experiment 2).

FIG. 7 depicts the normalized viable cell densities of cells expressing mAb3 cultivated in shake flasks as a function of time in three different cell culture media (Experiment 3).

FIG. 8 depicts the viability of cells expressing mAb3 cultivated in shake flasks as a function of time in three different cell culture media (Experiment 3).

DETAILED DESCRIPTION OF THE INVENTION

Figure 1:
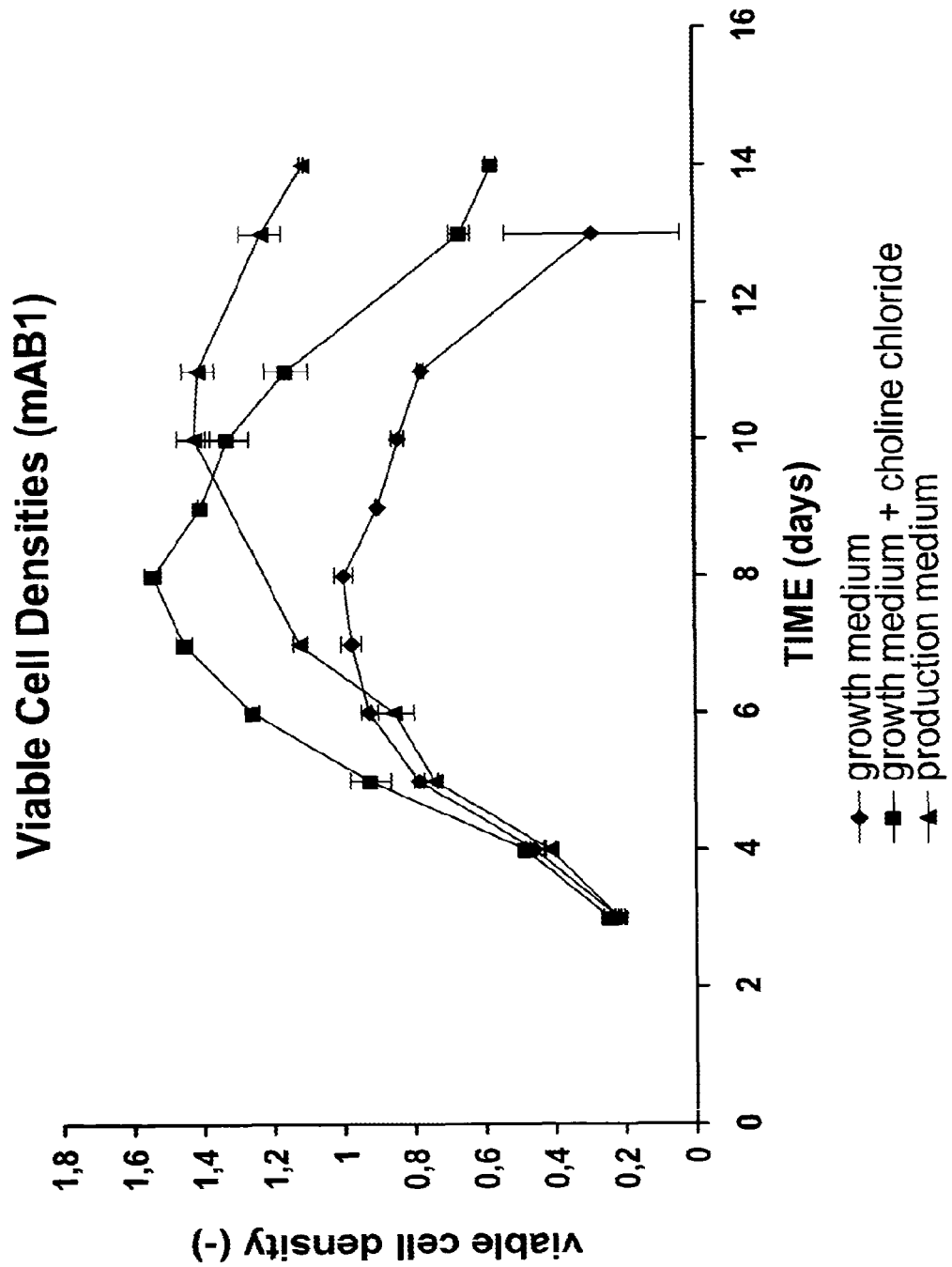
In FIG. 1 to FIG. 8, the three media are low choline growth medium (♦(diamond); control 1), production medium (▲(triangle); control 2) and high choline growth medium, i.e. low choline growth medium supplemented with an additional amount of 200 mg/l choline chloride (■(square)).

Conventional cell culture media that are used for cultivation of cells and the subsequent production of polypeptides from these cell cultures only contain low amounts of choline chloride. Only very few cell culture media described in the prior art contain moderate or even high amounts of choline chloride. However, those media have not been systematically investigated in terms of the role high amounts of choline chloride have on cell specific productivity, cell growth and product quality, especially when used during production phase.

According to the present invention, there is observed an unexpected improvement of the cell specific productivity (or polypeptide expression) when cultivating CHO cells using cell culture media as production media comprising high amounts of choline chloride as compared to media with lower amounts of choline chloride. It is demonstrated herein that even a growth medium when supplemented with high amounts of choline chloride can be surprisingly used as an effective production medium for cultivation of CHO cells during production phase thereby obtaining large amounts of polypeptide, preferably polypeptide obtained by recombinant polypeptide expression in cell cultures.

Although choline chloride is preferably used according to the present invention, other sources of choline, for instance choline hydroxide, choline tartrate/bitartrate, choline sulphate, choline phosphate or every other choline compound based on the use of a different counterion is also equally suitable for use in the cell culture media according to the present invention.

The use of the cell culture medium according to the present invention for production of polypeptides generally involves the cultivation of CHO cells for recombinant expression of polypeptides. It is preferred that the cell culture medium is used for large-scale production of polypeptides. Large-scale production of polypeptides relates to the amounts typically required for the industrial production of recombinant polypeptides used for preparation of therapeutically active biopharmaceuticals. Cell cultures of at least 500 L volume, at least 1000 L, least 5000 L or ever higher volumes typically represent large-scale production applications.

The amount of choline chloride in the cell culture medium according the present invention used for polypeptide production is significantly higher than the choline chloride content known from previously used cell culture media used for the polypeptide production at a large scale.

Accordingly, the present invention suitable for the production of a recombinant polypeptide using CHO cells comprising high content of choline chloride, such as 60 mg/L or higher, 80 mg/L or higher, 160 mg/L or higher, 200 mg/L or higher or even 220 mg/L or higher. The content of the choline chloride in the cell culture medium is limited to 2500 mg/L, 1000 mg/L, 840 mg/L, 500 mg/L or even 300 mg/L. Choline chloride may be present at a concentration of about 240 mg/L.

The higher the choline chloride concentration, the higher are the costs for the medium. Thus, too high choline chloride concentrations are disadvantageous from a cost perspective. Furthermore, the choline chloride content contributes to the osmolality of the medium. Too high choline chloride concentrations may be disadvantageous since they may lead, together with the other media components, to a total osmolality which is higher than desired. In particular in fed batch processes it is not desirable to use too high starting osmolalities as this may impose limitations on the feedings strategy.

For the above reasons, the inventors believe that optimal choline chloride concentrations are within the limits as set out herein.

If choline compounds other than choline chloride are used, they are employed in equivalent concentrations. Equivalent concentrations means that molar concentrations of choline are achieved which are in the same ranges as achieved when choline chloride is used at concentrations within the above ranges.

According to the first aspect of the present invention, the cell culture medium comprises only a limited content of amino acids expressed by the total concentration of amino adds. More in particular, the cell culture medium according to the first aspect of the invention is characterised by a total concentration of amino acids of from 20 to 57mmol/L. The total amino acids concentration can be above 25 mmol/L, above 30 mmol/L, above 35 mmol/L, or even above 40 mmol/L. Further, the total amino acids concentration can be below 54 mmol/L. The total amino acids concentration can for instance be about 51 mmol/L.

At the same time, the choline chloride concentration is as stated above, i.e. in the range of 60 mg/L to 2500 mg/L, with preferred ranges and values also as stated above.

The cell culture medium according to the first aspect of the present invention can be used in particular as production medium in order to achieve high cell growth, high viable cell densities and high polypeptide titer during the production phase. Further, higher product quality of the recombinant product is achieved, particularly in terms of less aggregation and/or better posttranslational modifications, such as improved glycosylation pattern.

The role of the amino acid glutamine for growth of cell cultures and resulting polypeptide productivity has been subject to extensive studies in recent years. If has been found that glutamine is not only an important building block for polypeptide synthesis but also represents a primary energy source for mammalian cells. Accordingly, high concentrations of glutamine have been usually included in cell culture media used for the polypeptide production. High amounts of glutamine in cell culture media are important for cell growth and polypeptide expression, particularly at industrial scale.

Nevertheless, glutamine metabolism results in decomposition of glutamine and the accumulation of ammonium ions, which is known as a by-product being toxic for cell growth and polypeptide production. Therefore, it is desirable to limit the amount of glutamine in cell cultures. Several glutamine replacement agents have been suggested in the prior art, for instance glutamic acid. However, it has been described that replacement of glutamine with glutamic acid in fed-batch processes leads to less by-product formation but also lower productivity (Doverskog et. al., J. Biotechnol., 1997 59, 103-115). Therefore, cell culture media containing reduced amounts of glutamine while still allowing high cell growth and polypeptide productivity are desirable.

It has been found that the addition of high amounts of choline chloride allows for the use of media comprising reduced amounts of glutamine as compared to some known media, especially during production phase, while the productivity of the cells remains largely unaffected.

Thus, in accordance with the first aspect of the present invention there is provided a cell culture medium further comprising an optional amount of glutamine which is significantly reduced when compared to media from the prior art. The cell culture media can be also free of glutamine replacement agents like glutamic acid or the like. The cell culture medium optionally comprises glutamine in a concentration of 500 to 1400 mg/L, 800 to 1400 mg/L, or 900 to 1200 mg/L.

At the same time, the choline chloride concentration is as stated above, i.e. in the range of 60 mg/L to 2500 mg/L, with preferred ranges and values also as stated above. Further, the total concentration of amino acids in the cell culture medium is at the same time from 20 to 57 mmol/L, with preferred ranges and values also as stated above.

According to another optional modification of the first aspect of the present invention, the respective amounts of individual amino acids are as defined below.

Such moderate amounts of amino acids are still higher than the amounts of amino acids contained in conventional cell culture media like DMEM or RPMI but at the same time significantly lower than the amounts of amino acids contained in typical production media used for large scale production.

Increased amounts of amino acids in production media are considered to be important for high productivity and high product quality, especially when the polypeptide production is carried out at larger scale or even industrial scale. It has now been found that the presence of high amounts of choline chloride allows limiting the amounts of individual amino acids, especially in cell culture media used during production phase.

The content of individual amino acids in the cell culture medium according to this optional modification of the first aspect of the present invention comprises the following amino acids in the following amounts expressed in mmol/l:

| | |
|---|---|
| Arginine | 4.0-6.0, preferably 4.5-5.5 |
| Asparagine | 3.0-6.0, preferably 4.0-5.5 |
| Aspartic acid | 2.5-4.0, preferably 3.0-3.6 |
| Glycine | 0.3-0.8, preferably 0.5-0.7 |
| Histidine | 0.6-1.0, preferably 0.7-0.9 |
| Isoleucine | 2.0-5.0, preferably 3.0-4.0 |
| Leucine | 3.0-7.0, preferably 3.5-6.0 |
| Lysine | 2.0-4.0, preferably 2.5-3.5 |
| Methionine | 1.0-1.5, preferably 1.2-1.4 |
| Phenylalanine | 1.0-2.0, preferably 1.3-1.8 |
| Proline | 2.5-6.0, preferably 3.0-5.5 |
| Serine | 3.0-8.0, preferably 4.0-7.0 |
| Threonine | 2.0-3.5, preferably 2.5-3.1 |
| Tryptophane | 0.4-1.0, preferably 0.5-0.8 |
| Valine | 2.5-5.0, preferably 3.0-4.5 |
| Glutamine | 6.0-10.0, preferably 7.5-9.0 |
| Tyrosine | 1.0-2.0, preferably 1.2-1.8 |
| Cystine | 0.5-1.0, preferably 0.6-0.8 |

At the same time, the choline chloride concentration is as stated above, i.e. in the range of 60 mg/L to 2500 mg/L, with preferred ranges and values also as stated above. Further, the total concentration of amino acids in the cell culture medium is at the same time from 20 to 57 mmol/L, with preferred ranges and values also as stated above.

Due to the high content of choline chloride, the respective amounts of amino acids can be significantly lower than the amounts used in other cell culture media used for the large scale production of polypeptides. In other words, the addition of high amounts of choline chloride allows significantly reducing the amount of most of the amino acids without deterioration of cell growth, cell viability and polypeptide titer. This has the technical advantage that cell culture media with lower concentration of most of the included amino acids can be used thereby avoiding precipitation problems for less soluble cell culture media components. Further, significant cost reductions with respect to the cell culture media are achieved although the overall quality and yield of polypeptide product are not affected or could even be improved. As described below, the aggregation of the recombinant polypeptide product could be reduced by use of the cell culture media according to the present invention. Additionally, better posttranslational modifications like improved glycosylation pattern or other protein quality attributes like lower aggregation of the recombinant polypeptide have also been obtained. In some cases, modification of the cell culture media as disclosed by the present invention even helps to improve the cell viability and cell growth as well as the resulting polypeptide titer.

The term "cell culture medium" refers to an aqueous solution of nutrients which can be used for growing cells over a prolonged period of time. Typically, cell culture media include the following components: A source of energy, which will be usually a carbohydrate compound, preferably glucose, amino acids, preferably the basic set of amino acids, including all essential and non-essential amino acids, vitamins and/ or other organic compounds which are required at low concentrations, free fatty acids, and inorganic compounds including trace elements, inorganic salts, buffering compounds and nucleosides and bases.

The term "growth medium" refers to a cell culture medium which is normally used during expansion phase of the overall production process. The expansion phase is the first period of the overall cultivation/production process which is predominantly characterized by high cell growth and less polypeptide production. The expansion phase serves the purpose of expanding the cells, which means generating an adequate number of cells which are in the exponential growth phase to inoculate a production bioreactor.

The term "production medium" refers to a cell culture medium which is normally used during production phase of the overall production process. The production phase is a second phase of the overall cultivation/production process which serves the purpose of producing high amounts of product. During the production phase the cells should be maintained in viable and productive mode as long as possible.

The use of cell culture media in the field of pharmaceutical industry, for instance for the production of therapeutically active recombinant polypeptides, does generally not allow the use of any material of animal origin due to safety and contamination issues. Therefore, the cell culture medium according to the present invention is preferably a serum- and/or protein-free medium. The term "serum-and/or protein-free medium" represents a fully chemically defined medium, containing no additives from animal source like tissue hydrolysates, fetal bovine serum or the like. Further, proteins, especially growth factors like insulin, transferrin or the like are also preferably not added to the cell culture according to the present invention. Preferably, the cell culture medium according to the present invention is also not supplemented with a hydrolysed protein source like soybean, wheat or rice peptone or yeast hydrolysate or the like.

The cell culture medium according to the present invention can be used in various cell culture processes. Cultivation of cells can be carried out in adherent culture, for instance in monolayer culture or preferably in suspension culture.

Large scale cultivation of cells can be used for instance by the various fermentation processes established in industrial biotechnology. Discontinuous and continuous cell culture processes, like perfusion and chemostat, can be utilized using the cell culture media according to the present invention. Discontinuous processes, including repeated fed-batch and repeated batch, are one preferred embodiment.

The batch cell culture includes fed-batch culture or simple batch culture. The term "fed batch cell culture" refers to cell culture wherein cells and cell culture medium are supplied to the culturing vessel initially and additional culture nutrients are fed continuously or in discrete increments to the culture during the culturing process with or without periodic cell and/or product harvest before termination of the culture. The term "simple batch culture" relates to a procedure in which all components for cell culturing including the cells and the cell culture medium are supplied to the culturing vessel at the start of the culturing process.

The cells cultivated in the cell culture medium according to the present invention are CHO cells.

The polypeptides that can be produced from the cell cultures and the cell culture media according to the present invention are not limited. The polypeptides can be recombinant or not recombinant. The term "polypeptide" as used herein encompasses molecules composed of a chain of more than two amino acids joined by peptide bonds; molecules containing two or more such chains; molecules comprising one or more such chains being additionally modified, e.g. by glycosylation. The term polypeptide is intended to encompass proteins.

The preferred class of polypeptides produced by cell cultures and the cell culture media according to the present invention are recombinant antibodies.

The term "antibody" is used in the broadest sense and specifically covers monoclonal antibodies (including full length monoclonal antibodies), polyclonal antibodies, multi-specific antibodies (e.g., bispecific antibodies), nanobodies, modified antibodies, subunits of antibodies, antibody derivatives, artificial antibodies, combinations of antibodies with proteins and antibody fragments sufficiently long to display the desired biological activity, The monoclonal antibodies as used herein may be human antibodies.

However, polypeptides other than antibodies can also be produced using cell cultures and the cell culture media according to the present invention, e.g. polypeptides like transmembrane proteins, receptors, hormones, growth factors, proteases, clotting and anti-clotting proteins, inhibitor proteins, interleukins, transport factors, fusion proteins and the like. The cell culture medium can also be used for the production of viruses.

The products obtained from such cell culture processes can be used for the preparation of pharmaceutical preparations. The term "pharmaceutical preparation" indicates a composition suitable or adapted to for administration to a mammal especially a human. In addition, the protein(s) according to the invention can be administered together with other components of biologically active agents such as pharmaceutically acceptable surfactants, recipients, carriers, diluents and vehicles.

The presence of high amounts of choline chloride in the cell culture medium according to the present invention allow the reduction of the content of amino acids in the cell culture medium without negatively affecting the medium's ability to support growth of cells at high densities and enabling high polypeptide titer at the same time. This effect is especially important for the production phase of the overall production process.

Most of the experiments have even revealed that even better performance parameters are achieved by the cell culture medium according to the present invention when compared to conventional production media comprising higher concentrations of selected amino acids combined with only low amounts of choline chloride.

While not being bound to a certain theory, it is assumed that the concentration of the phospholipid precursor choline is linked to the amount of the essential cell membrane component phosphatidylcholine, which is, besides other phospholipids, necessary to preserve the integrity and the functionality of cell membranes. It may be assumed that the cells growing in a medium with low choline content are limited in this substrate during the cultivation process end thereby in phosphatidylcholine, even if choline is a non-essential media component and the cells should be able to synthesise it independently. However, an inactive or limited pathway could be the reason that limited amounts of choline are available to produce sufficient amounts of phosphatidylcholine. This could lead in an "abnormal" composition of membranes, especially membranes of the endoplasmatic reticulum and of the Golgi complex. This could negatively influence the function of these membranes and reduce polypeptide expression rates or polypeptide transport within the cells. Inhibition of the polypeptide transport from the Golgi complex towards the plasma membrane in phosphatidylcholine-depleted CHO cells was shown by Testerink et al. (2009: Journal of Lipid Research, Vol 50, 2182-2192). This defect could be rescued by addition of exogenous phosphatidylcholine.

Several important advantages result from the specific composition of the cell culture media according to the present invention.

First, the reduction of the total content of amino acids in the cell culture media according to the present invention allows performing the cell culture processes with similar or even improved technical performance parameters in terms of cell growth, viable cell densities as well as polypeptide productivity, while, at the same time the reduction of the total content of amino acids or of some selected amino acids in the cell culture leads to a better overall economical balance of the production process due to cost reduction as far as the cell culture medium is concerned.

Second, the cell culture media according to the present invention avoid the risk of precipitation of components contained in the cell culture medium, in particular hydrophobic amino acids contained in the medium at relatively high concentrations. This is in particular advantageous during storage of media. For these components reduced concentrations help to avoid deterioration of supply with essential substrate during growth of the cells and production of polypeptide. This is especially beneficial during the production phase of the overall production process.

Third, the cell culture media according to the present invention allow the production of recombinant polypeptides with higher quality. The aggregation of the formed polypeptide is reduced, the cells are able to produce polypeptide with better posttranslational modifications and glycosylation patterns are also improved.

Aggregation of the formed polypeptide during recombinant expression is a technical problem that leads to reduced product yields. Moreover, aggregation makes it more difficult to purify the functionally active polypeptide product.

Therefore, it is desirable to reduce aggregation of the formed polypeptide product as much as possible during the actual production process. It has been found that the cell culture media according to the present invention leads to reduced aggregation of recombinant polypeptide product when compered to typical production media.

Many polypeptides are subject to posttranslational modification, especially polypeptide glycosylation. The resulting polypeptides comprise covalently linked oligosaccharide chains. Glycosylation is known as an important mediator of polypeptide functionality. Therefore, the ability of a host cell system used for recombinant polypeptide production to properly mimic endogenous glycosylation structures is an important aspect of product quality. Therapeutic efficiency of a recombinant polypeptide can be strongly affected by improper polypeptide glycosylation due to immunogenic properties and reduced half-life in vivo after administration of incorrectly glycosylated polypeptides.

Generally mannosylation is considered a critical aspect in recombinant polypeptide production, especially in the field of recombinant antibodies. It is a general objective in recombinant polypeptide production to avoid high mannosylation of polypeptides. It is therefore an important objective to reduce high mannosylation during production of recombinant polypeptides as much as possible.

The cell culture media according to the present invention allow producing recombinant polypeptides with very low degree of high mannosylation. This technical effect is especially significant with respect to typical production media. For instance, the relative amount of high mannosylated recombinant polypeptide with high mannosylation of total amount of recombinant polypeptide obtained from expression using the cell culture media according to the present invention is preferably lowered by about 50% compared to the production medium.

Further, it has been surprisingly found that recombinant polypeptides obtained by using the cell culture media according to the present invention have higher percentages of β-galactosylation relative to the corresponding polypeptides obtained by using conventional growth media or production media.

A further advantage of the medium with high choline concentrations is that it allows to have only one medium for production and expansion phase, saving time and resources

EXAMPLES

The following experiments are intended to further illustrate the invention as defined in this application.
Description of the Cell Culture Media
The three following media are tested:
Low choline growth medium, i.e. with a content of choline chloride of 40 mg/L (control 1):
Production medium (control 2):
High choline growth medium, i.e. low choline growth medium supplemented with an additional amount of choline chloride of 200 mg/L resulting in a total content of choline chloride of 240 mg/L.

The first two media (low choline growth and production medium) are used for comparative purposes only, while the third medium with high content of choline chloride represents a medium according to the present invention.

The low choline growth medium is a typical medium designed for growth and proliferation of a cell culture. This medium allows cultivating cells until high densities of cells are reached, which is an important requirement for large-scale polypeptide production. However, the low choline growth medium is not designed for polypeptide production from cell culture because the content of many amino acids is low to moderate considering the total concentration of amino acids in the medium of 51.1 mmol/L.

The amino acid composition of the low choline growth medium is as follows:

| Amino acid | mg per l medium | Conc (mmol/L) |
|---|---|---|
| L-arginine, HCl | 1053 | 5.0 |
| L-aspargine monohydrate | 616 | 4.1 |
| L-aspartic acid | 461 | 3.5 |
| Glycine | 38 | 0.5 |
| L-histidine HCl $H_2O$ | 168 | 0.8 |
| L-isoleucine | 394 | 3.0 |
| L-leucine | 500 | 3.8 |
| L-lysine HCl | 622 | 3.4 |
| L-methionine | 180 | 1.2 |
| L-phenylalanine | 264 | 1.6 |
| L-proline | 368 | 3.2 |
| L-serine | 432 | 4.1 |
| L-threonine | 334 | 2.8 |
| L-tryptophan | 102 | 0.5 |
| L-valine | 375 | 3.2 |
| L-glutamine | 1170 | 8.0 |
| L-tyrosine | 278*) | 1.5 |
| L-cystine | 200*) | 0.8 |
| Total Content | | 51.0 |

*)L-tyrosine and L-cystine are added to the low choline growth medium using a stock solution in order to achieve the above indicate concentrations of tyrosine and cystine.

In contrast to the low choline growth medium, the second medium (production medium) is a medium useful for large scale polypeptide production using cell cultures. This production medium contains higher amounts of most of the amino acids (the total concentration of amino acids in the medium is 90.50 mmol/L) when compared to the low choline growth medium although the amounts of other components are basically identical.

The amino acid composition of the production medium used is as follows:

| Amino acid | mg per l medium | Conc (mmol/L) |
|---|---|---|
| L-arginine, HCl | 1053 | 5.0 |
| L-aspargine monohydrate | 1501 | 10.0 |
| L-aspartic acid | 461 | 3.5 |
| Glycine | 38 | 0.5 |
| L-histidine HCl $H_2O$ | 268 | 1.3 |
| L-isoleucine | 894 | 6.8 |
| L-leucine | 1200 | 9.2 |
| L-lysine HCl | 822 | 4.5 |
| L-methionine | 280 | 1.9 |
| L-phenylalanine | 464 | 2.8 |
| L-proline | 968 | 8.4 |
| L-serine | 1232 | 11.7 |
| L-threonine | 534 | 4.5 |
| L-tryptophan | 252 | 1.2 |
| L-valine | 776 | 6.6 |
| L-glutamine | 1169 | 8.0 |
| L-glutamic acid Na-salt hydrate | 182 | 1.2 |
| L-tyrosine | 423*) | 2.3 |
| L-cystine | 305*) | 1.3 |
| Total Content | | 90.7 |

The content of choline chloride in this comparative production medium is also significantly higher than in the low choline growth medium. It is important to note that known production media from the prior art usually contain much lower amounts of choline chloride. Therefore, the high content of choline chloride in the comparative production medium must be considered as an important difference to known production media from the prior art, which normally do not differ from known growth media in their content of choline chloride The third medium is a medium according to the present invention represented by the high choline growth medium, i.e. the low choline growth medium supplemented with 200 mg/l choline chloride resulting in an overall content of choline chloride of 240 mg/l. With the exception of the higher content of choline chloride, the third medium according to the present invention could be still considered as a typical growth medium.

The examples demonstrate the marked improvement achieved by high amounts of choline chloride in growth media like the low choline growth medium when used during production phase, rendering such growth media with high content of choline chloride not only vastly superior to low choline chloride-supplemented media in terms of cell growth, cell viability and polypeptide titer, but even superior to production media with equally high amounts of choline chloride in the same aspects. The addition of higher amounts of choline chloride helps to achieve better cell growth and viability and improved polypeptide titer in normal growth media.
Experimental Setup For the experiments a parental CHO cell line is used which is derived from the dhfr (+) CHO-K1 cell line ATCC CCL-61 (Kao et. al., Genetics, 1967, 55, 513-524; Kao at. al., PNAS, 1968, 60, 1275-1281; Puck et. al., J. Exp. Med., 1958, 108, 945-959) by adaptation to serum-free, protein-free media conditions. Three aliquots of this parental cell line are transfected to express three different monoclonal antibodies mAb1, mAb2, mAb3, respectively.

Shake Flask Experiments (Experiments 1 to 3)

All nine shake flasks (three for each experiment) are run under the same conditions, except for the medium. The conditions involve a fed-batch culture with two daily bolus feeds starting at days 3 and 5 with a feeding rate of 2 and 0.4% of the initial culture volume per day; a temperature shift from 36.5° C. to 33° C. at day 5; 10% $CO_2$ in the incubator; a shaking rate of 150 rpm (stroke radius=25 mm). The cell growth/viability of the cells as well as the resulting titer of recombinant antibody expressed are determined.

a) Experiment 1

Figure 2:
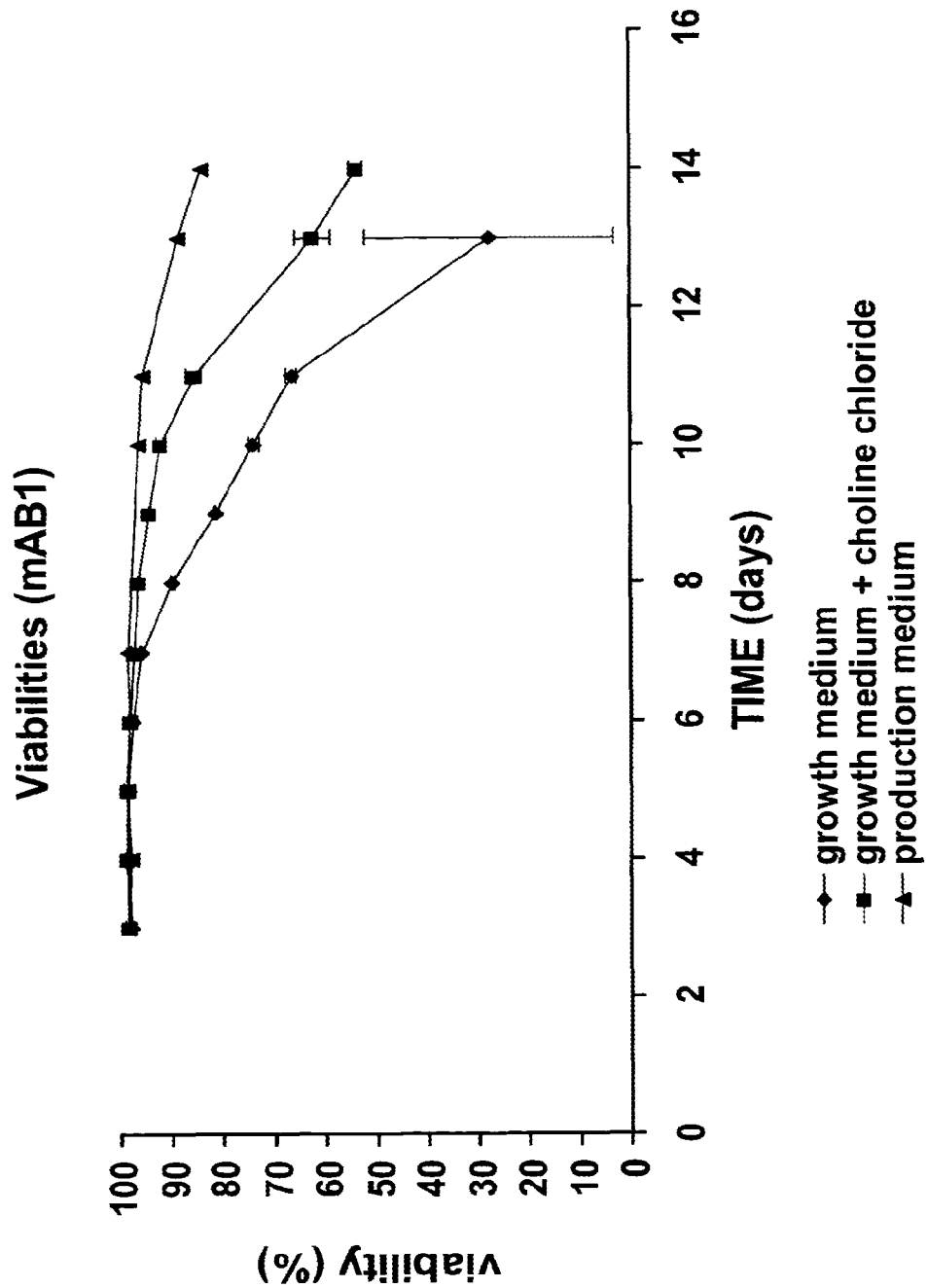

FIGS. 1 and 2 show the results obtained for the cells expressing mAb1 cultivated in Experiment 1 in terms of cell growth and viability.

As illustrated in FIGS. 1 and 2, the inventive medium with high content of choline chloride (the high choline growth medium) shows a 53% increase in the maximum viable cell density and a slower decline of the viability when compared to the low choline growth medium having low content of choline chloride.

Figure 3:
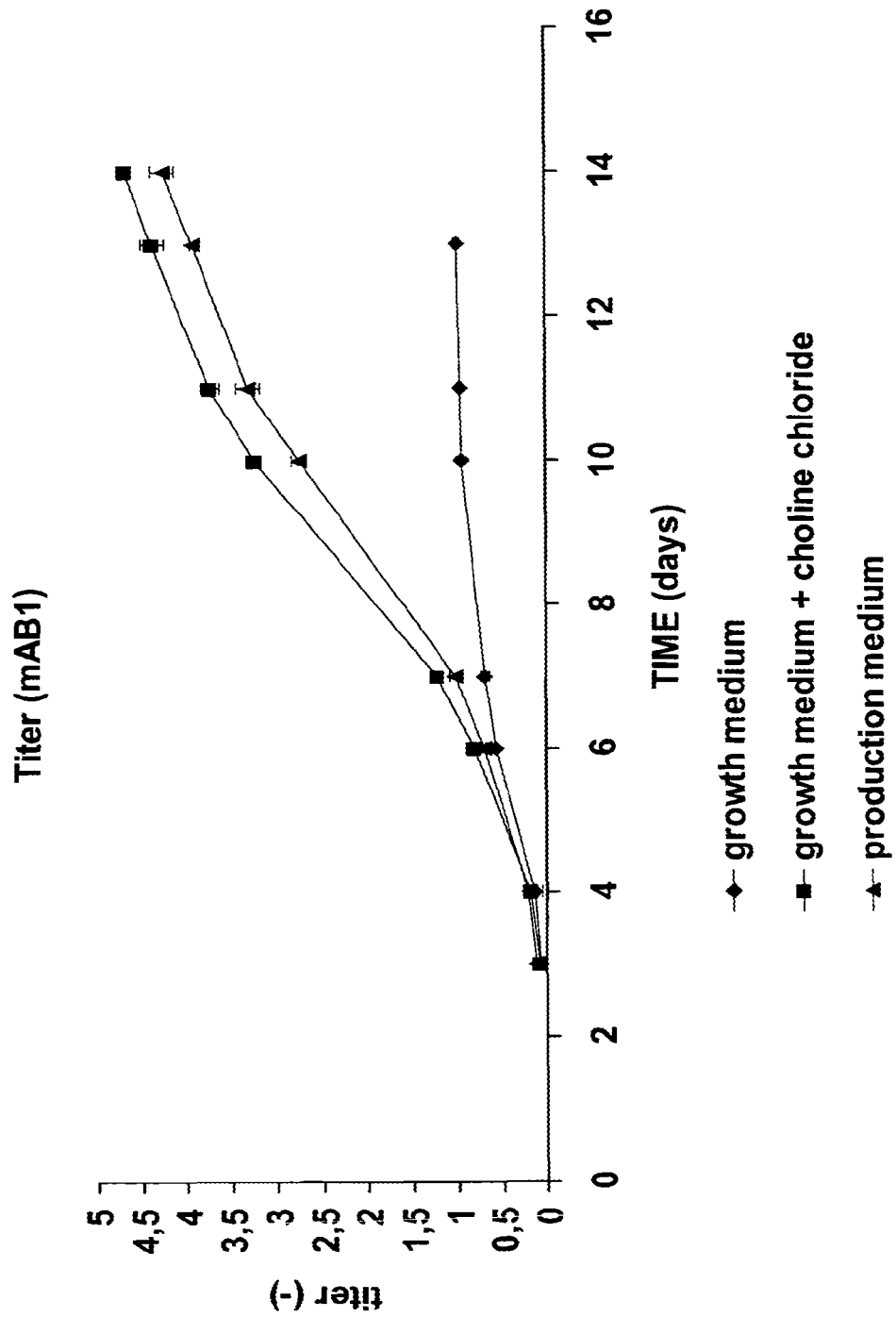

FIG. 3 shows the results obtained for the cells cultivated in Experiment 1 in terms of polypeptide titer As illustrated by FIG. 3, the polypeptide titer of recombinant antibody obtained in the inventive medium with high content of choline chloride (the high choline growth medium) shows an increase in polypeptide titer of 330% at day 13 compared to the low choline growth medium, which has only low content of choline chloride and represents a typical growth medium only.

FIG. 3 also reveals that the inventive medium with high content of choline chloride even allows achieving a polypeptide titer that is slightly higher than the titer obtained from the production medium.

b) Experiment 2

Figure 4:
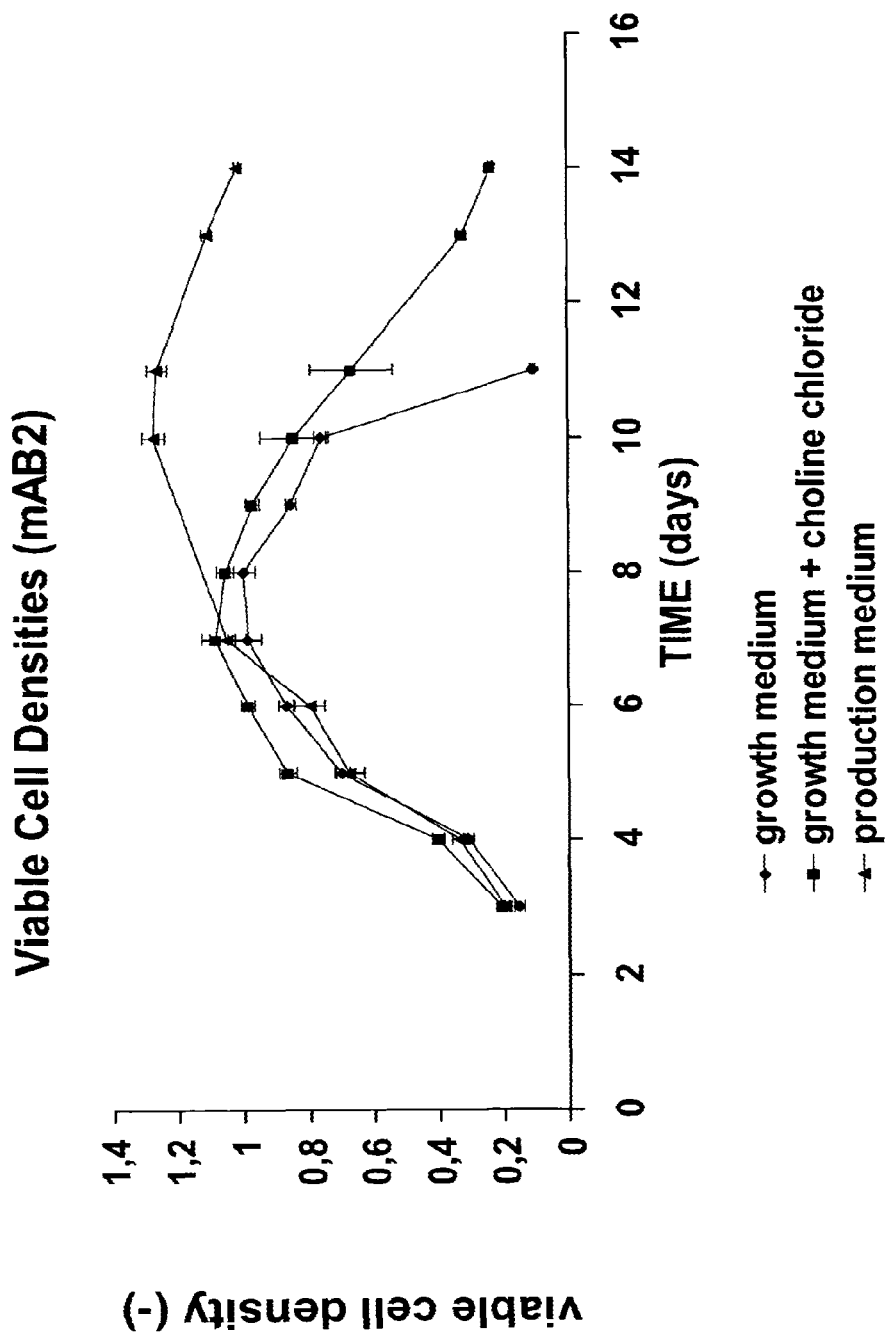
Figure 5:
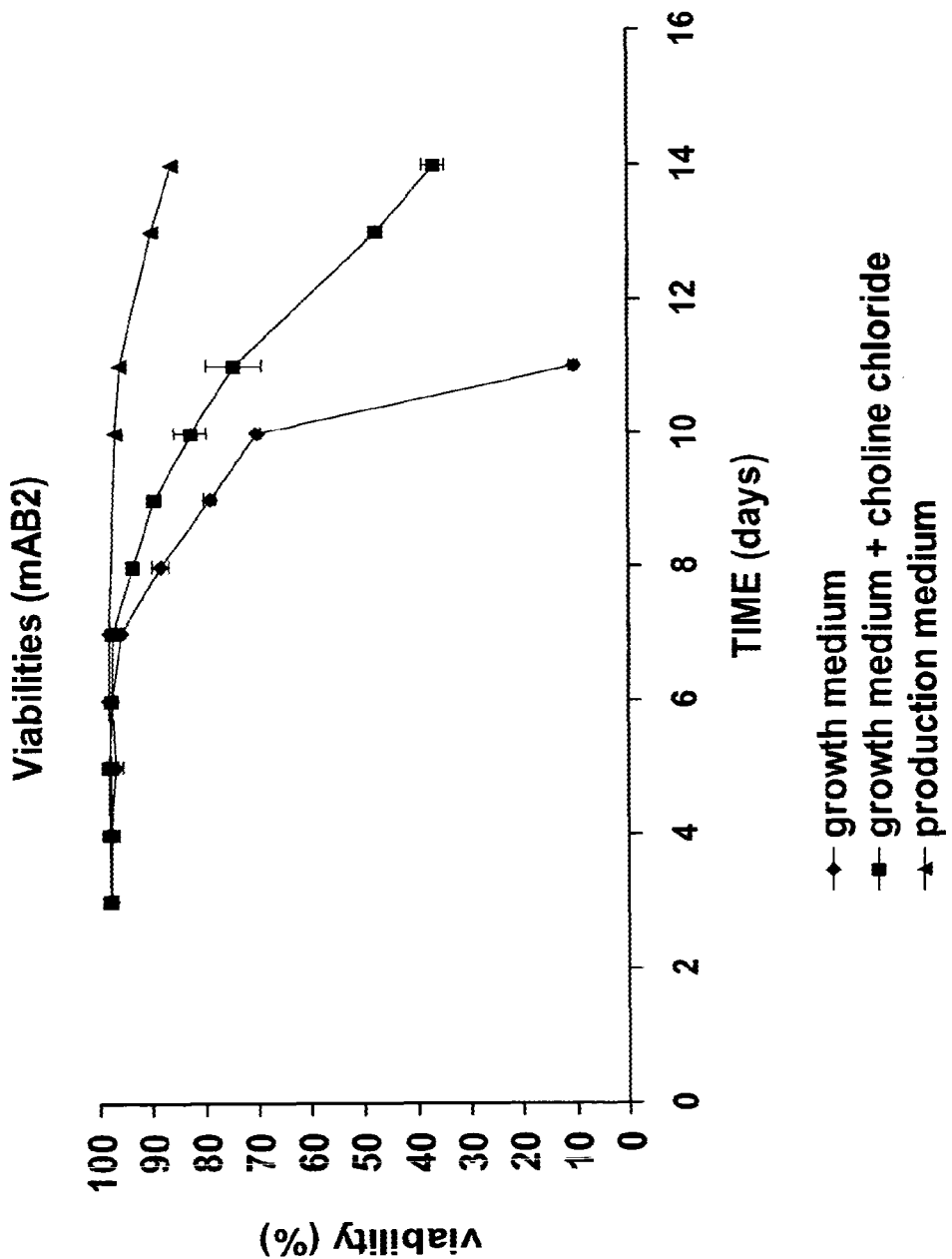

FIGS. 4 and 5 show the results obtained for the cells expressing mAb2 cultivated in Experiment 2 in terms of cell growth and viability As illustrated by FIGS. 4 and 5, the inventive medium with high content of choline chloride (the high choline growth medium) has only small influence on cell growth but gives significantly higher viabilities at the end of the process when compared with the low choline growth medium, which has only low content of choline chloride.

Figure 6:
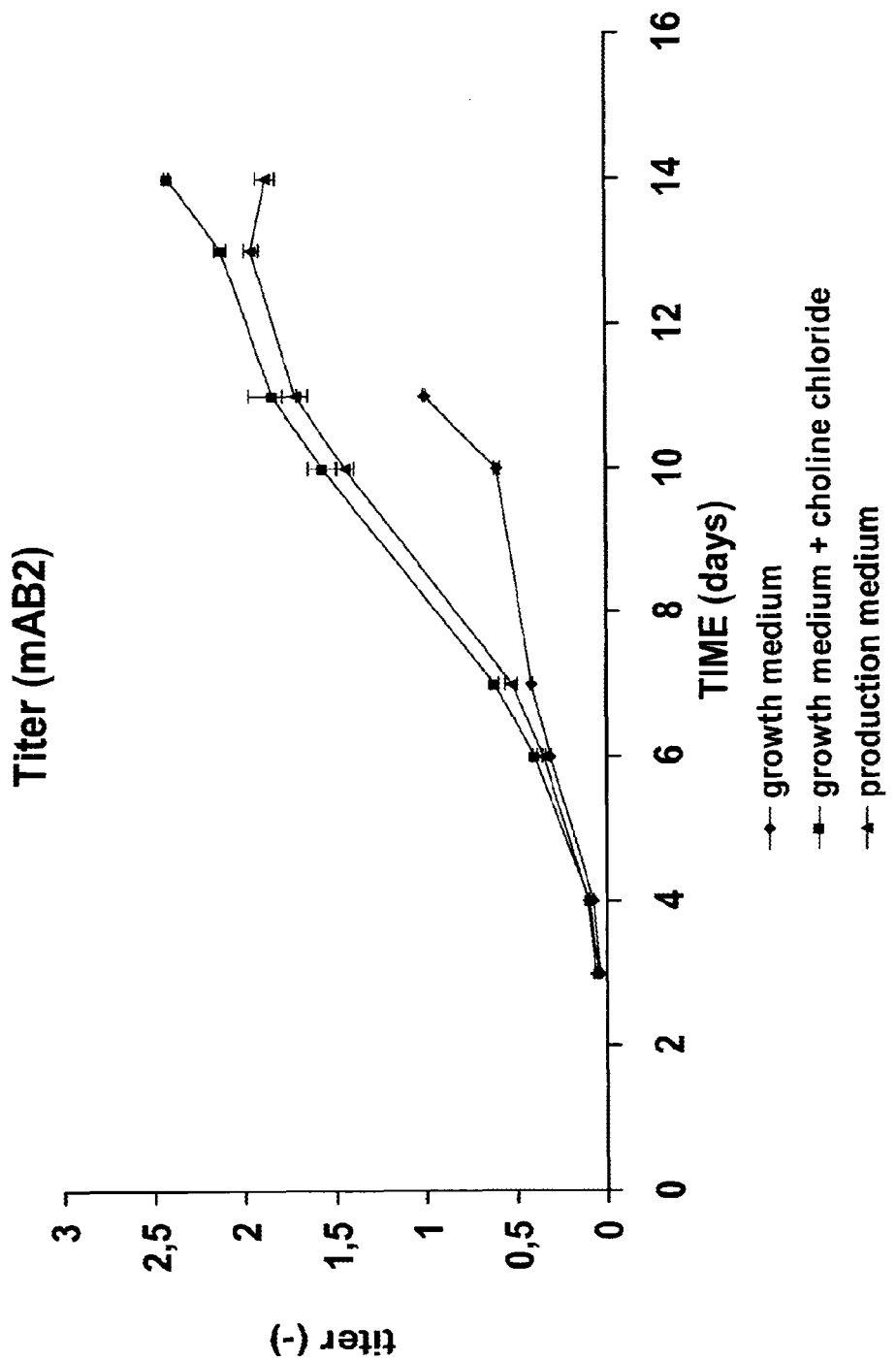

FIG. 6 shows the results obtained for the cells cultivated in Experiment 2 in terms of polypeptide titer.

FIG. 6 reveals a 85% increase of polypeptide titer at day 11 for the cell culture medium according to the present invention when compared to the low choline growth medium. Further, the polypeptide titer obtained in the cell culture medium according to the present invention is even higher when compared with the polypeptide titer obtained in the production medium having equally high content of choline chloride.

c) Experiment 3

Figure 7:
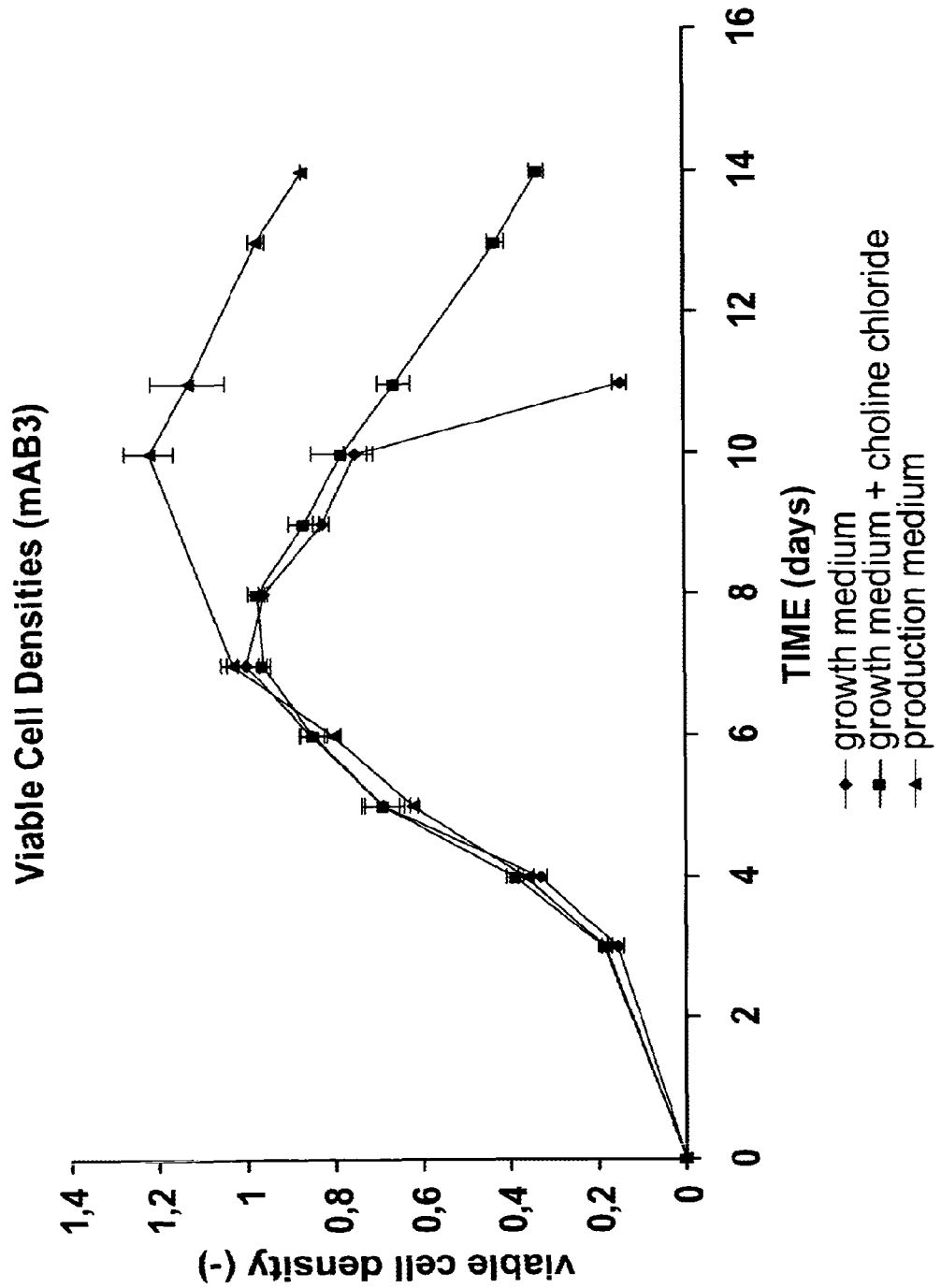
Figure 8:
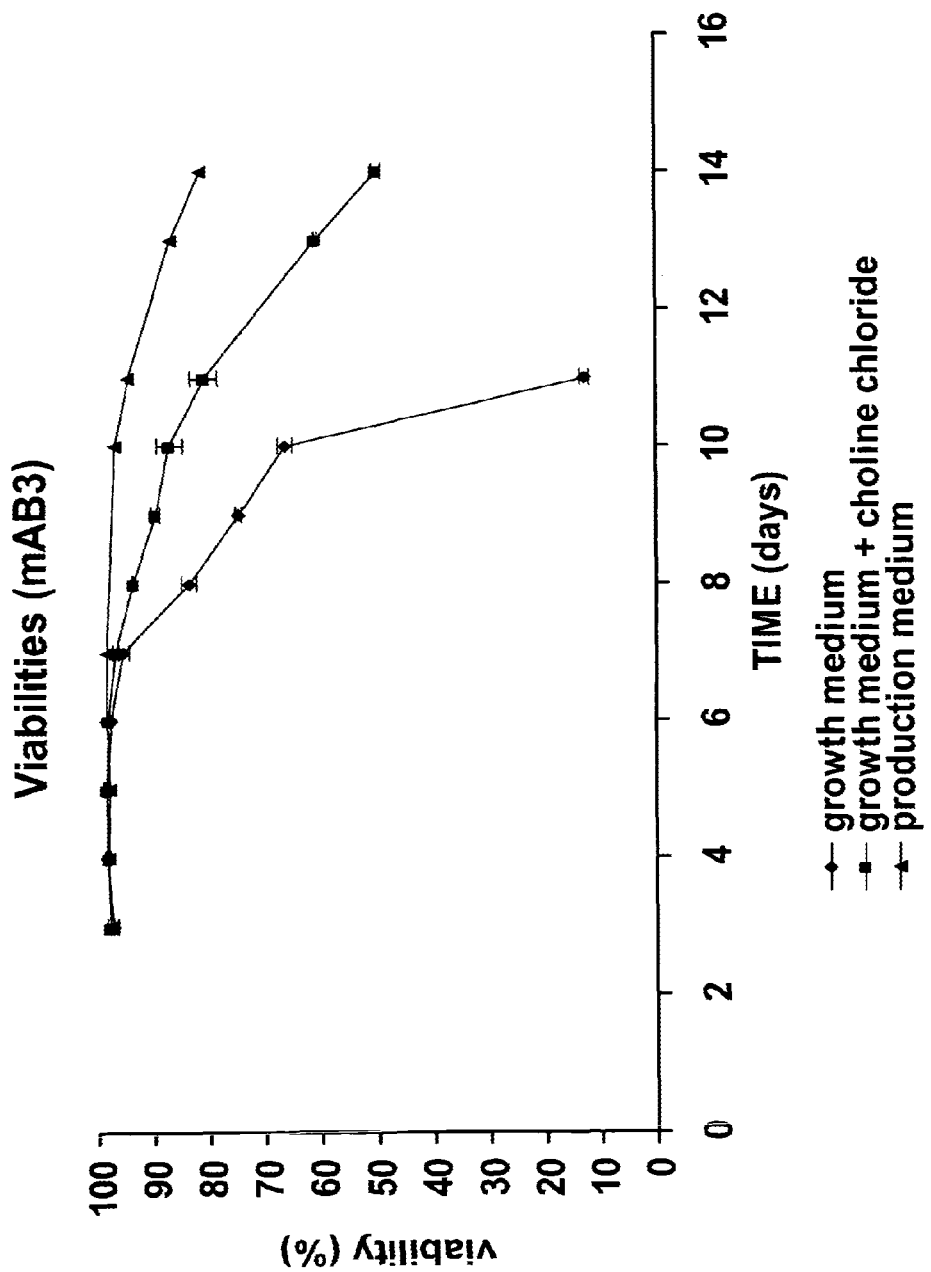

FIGS. 7 and 8 show the results obtained for the cells expressing mAb3 cultivated in Experiment 3 in terms of cell growth and viability.

As illustrated by FIGS. 7 and 8, higher cell viabilities at the end of the cultivation process are obtained with the medium according to the present invention when compared with the comparative cell culture medium (the low choline growth medium) comprising only low amounts of choline chloride.

Figure 9:
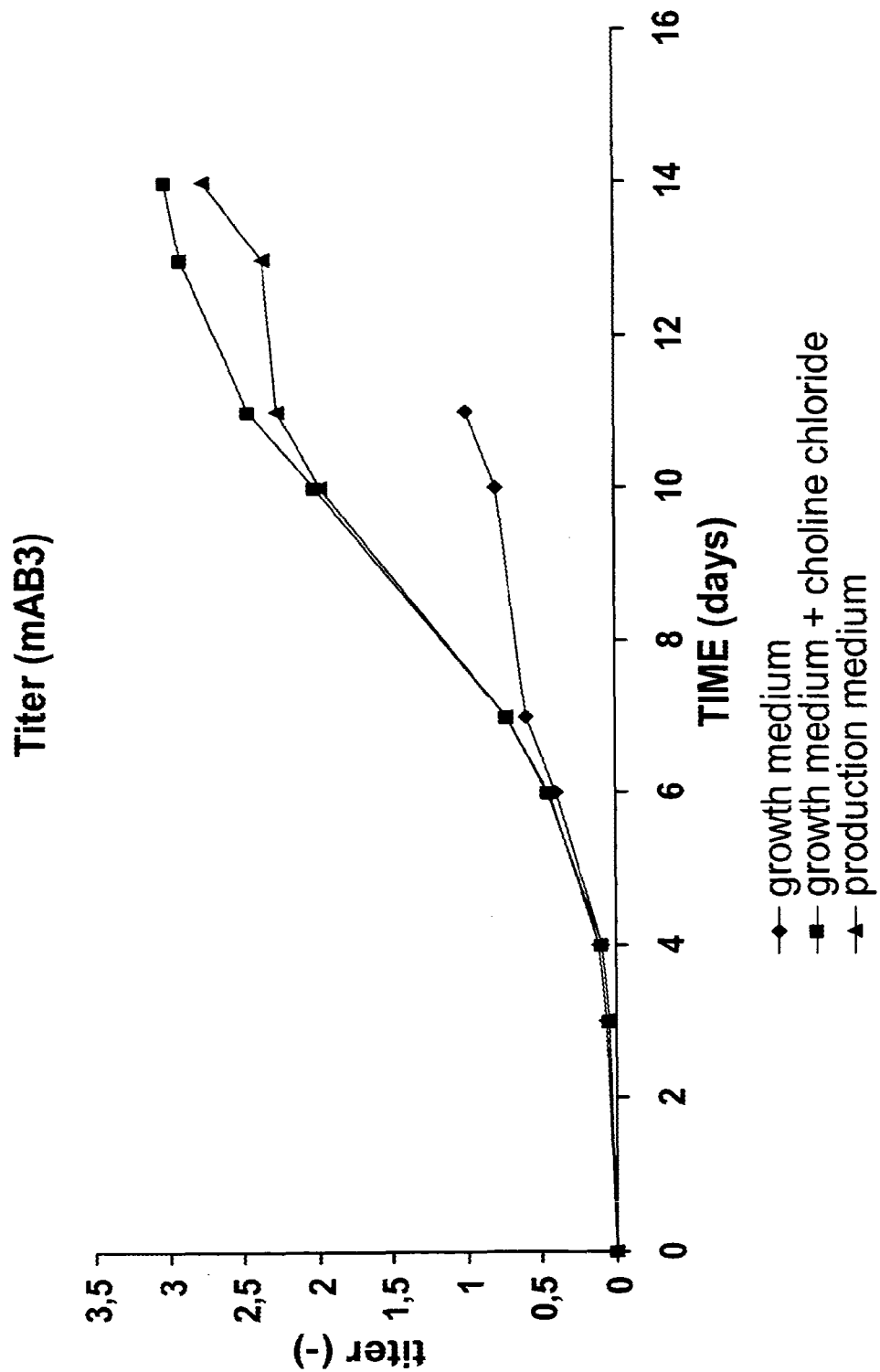
FIG. 9 depicts the normalized polypeptide titer obtained after cultivation of cells expressing mAb3 in shake flasks as a function of time for three different media (Experiment 3).

FIG. 9 shows the results obtained for the cells cultivated in Experiment 3 in terms of polypeptide titer.

FIG. 9 reveals that the polypeptide titer obtained in the cell culture medium according to the present invention is increased by 145% at day 11 when compared to the comparative medium, the low choline growth medium. The polypeptide titer for the cell culture medium according to the present invention is even slightly higher than the titer obtained by using the production medium with high content of choline chloride.

It has been further experimentally confirmed that the use of higher concentrations of choline chloride in the production medium did not result in improved cell growth or polypeptide titer when compared to the use of the production medium having the standard amount of choline chloride of 240 mg/L.

The following additional experiments are carried out in order to determine the influence of cell culture medium on polypeptide product quality. In particular, product is analysed in order to determine the influence of the media on aggregation and on glycosylation.

Figure 10:
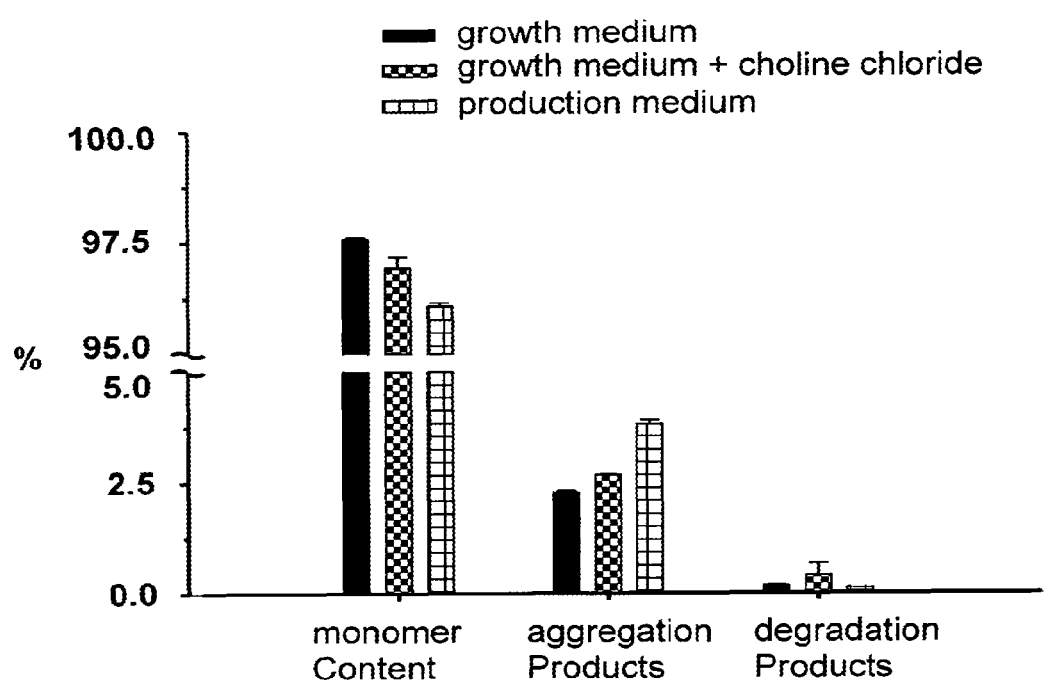
FIG. 10 depicts the aggregation rate of mAb3 produced after seven days of cultivation in shake flasks. The aggregation rate is measured by size-exclusion chromatography (SEC). Error bars are standard deviations of three biological replicates.

FIG. 10 shows the percent aggregation rate of recombinant antibody product, relative to the total amount of recombinant antibody. The aggregation rate in the cell culture medium according to the present invention is reduced by more than 30% relative to the production medium.

The expression of mAb3 in different cell culture media followed by analysis of the glycosylation pattern of the recombinant antibodies shows that the growth medium according to the present invention with a high content of choline chloride leads to a recombinant antibody with a low total amount of recombinant product comprising high mannosylation, which represents an unwanted glycosylation pattern. Using a medium according to the invention leads to a reduction of more than 55% in terms of high mannosylation compared to using the production medium.

Bioreactor Fed-Batch Runs (Experiment 4)

The following experiment is the fed-batch run in the bioreactor. It corresponds to the above Experiment 3. Cells expressing mAb3 were used. The conditions are as follows: 2 L starting volume; continuous feeding of two different feeding solohons starting day 3 and 5 with a feeding rate 2 and 0.4% of the initial culture volume per day; a temperature shift from 36.5° C. to 33° C. at day 5; $pO_2$=30%; pH=6.9 (deadband 0.1); controlled with $CO_2$ and 0.5M NaOH; agitation rate=300 rpm.

Figure 11:
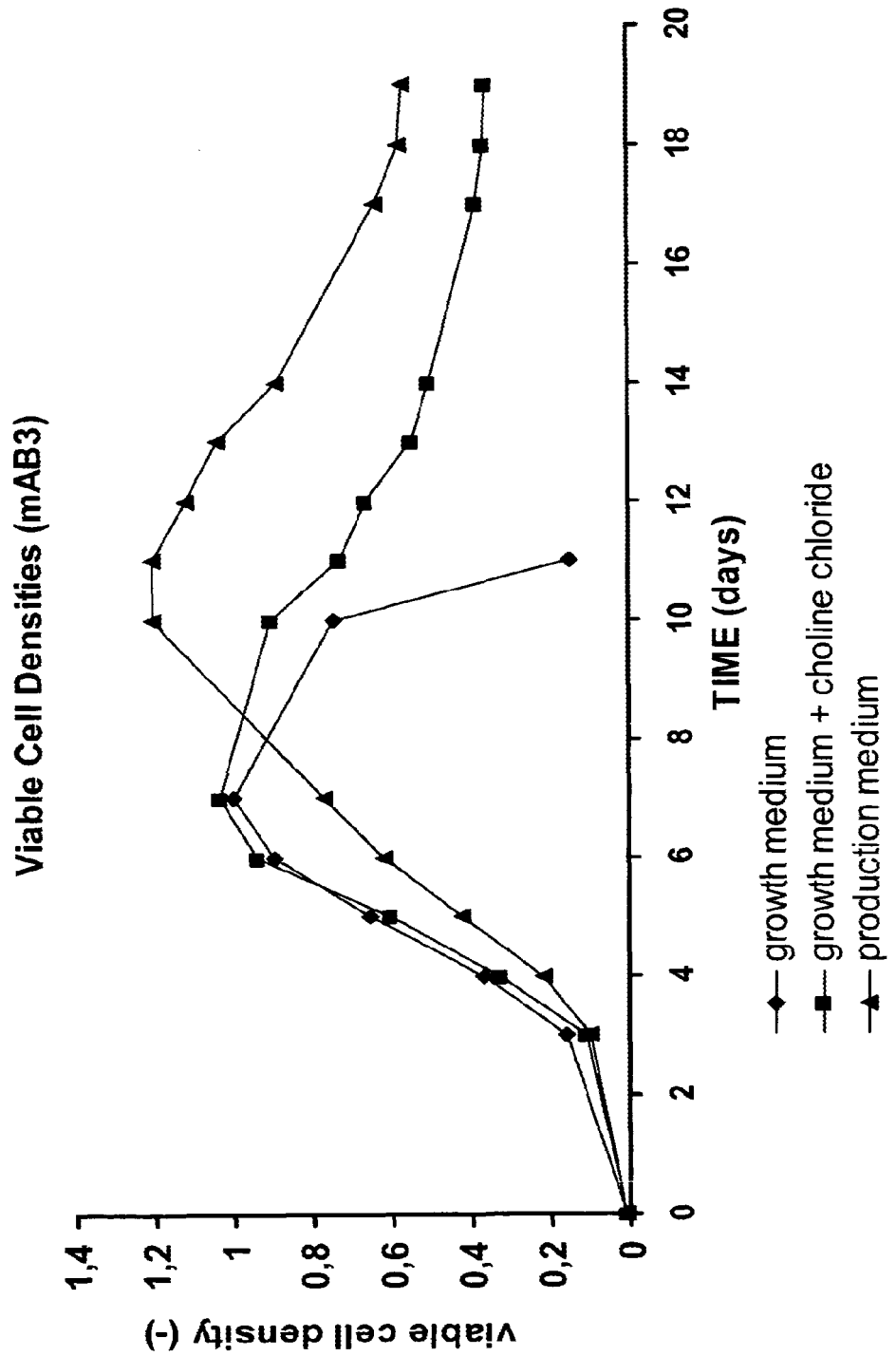
FIG. 11 depicts the normalized viable cell densities of cells expressing mAb3 cultivated in a fed-batch run in a bioreactor as function of time in three different cell culture media (Experiment 4).
Figure 12:
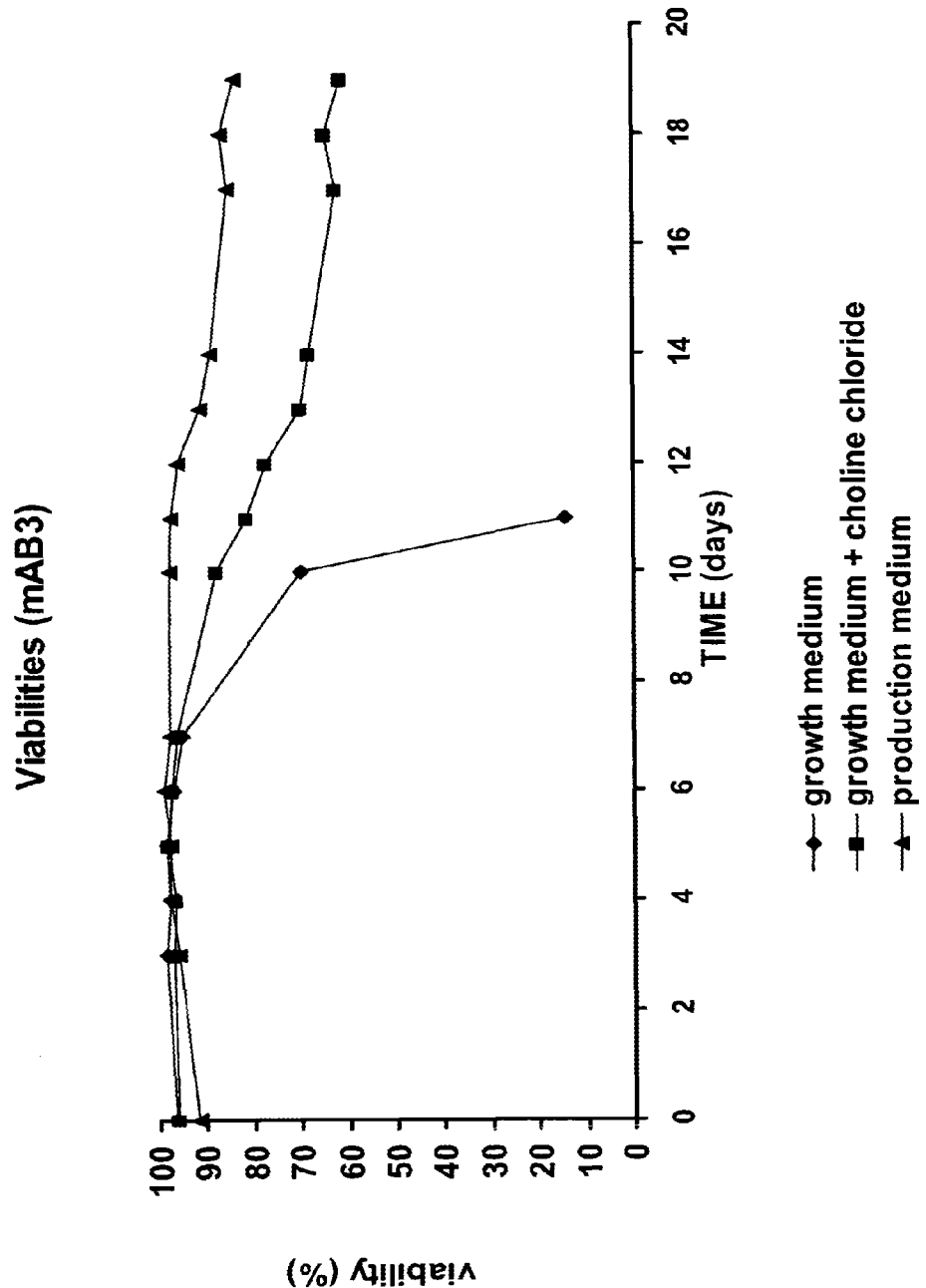
FIG. 12 depicts the viability of cells expressing mAb3 cultivated in a fed-batch run in a bioreactor as function of time in three different cell culture media (Experiment 4).

FIGS. 11 and 12 show the results obtained for viable cell density and viability percentage of cells in Experiment 4 carried out as fed-batch run in a bioreactor.

Regarding the cell growth and viability of the cells the results from the fed-batch run in the bioreactor are consistent with the results obtained in the shake flask experiments. That is, the fed-batch run in the bioreactor basically confirms the results obtained in the shake flask experiments.

Like in the shake flask experiment peak viable cell densities achieved in production medium were slightly higher compared to the inventive cell culture medium (the high choline growth medium) with high content of choline chloride. However, the percentage of viability stays at a significantly higher level when the inventive cell culture medium, i.e. the medium supplemented with high content of choline chloride is used compared to the non-supplemented growth medium having only low content of choline chloride.

Figure 13:
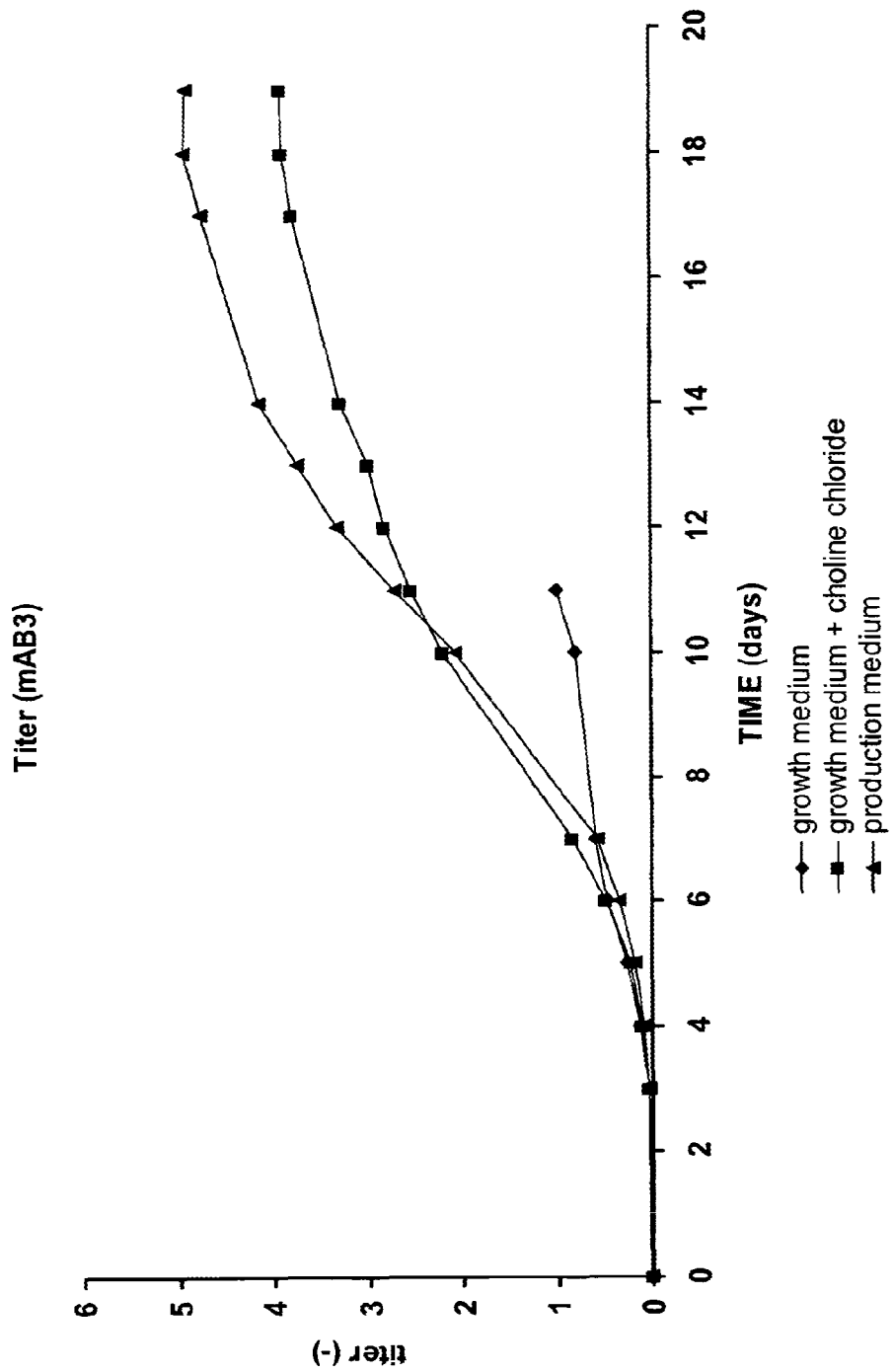
FIG. 13 depicts the normalized polypeptide titer obtained using cells expressing mAb3 in a fed-batch run in a bioreactor as a function of time using three different media (Experiment 4).
Figure 14:
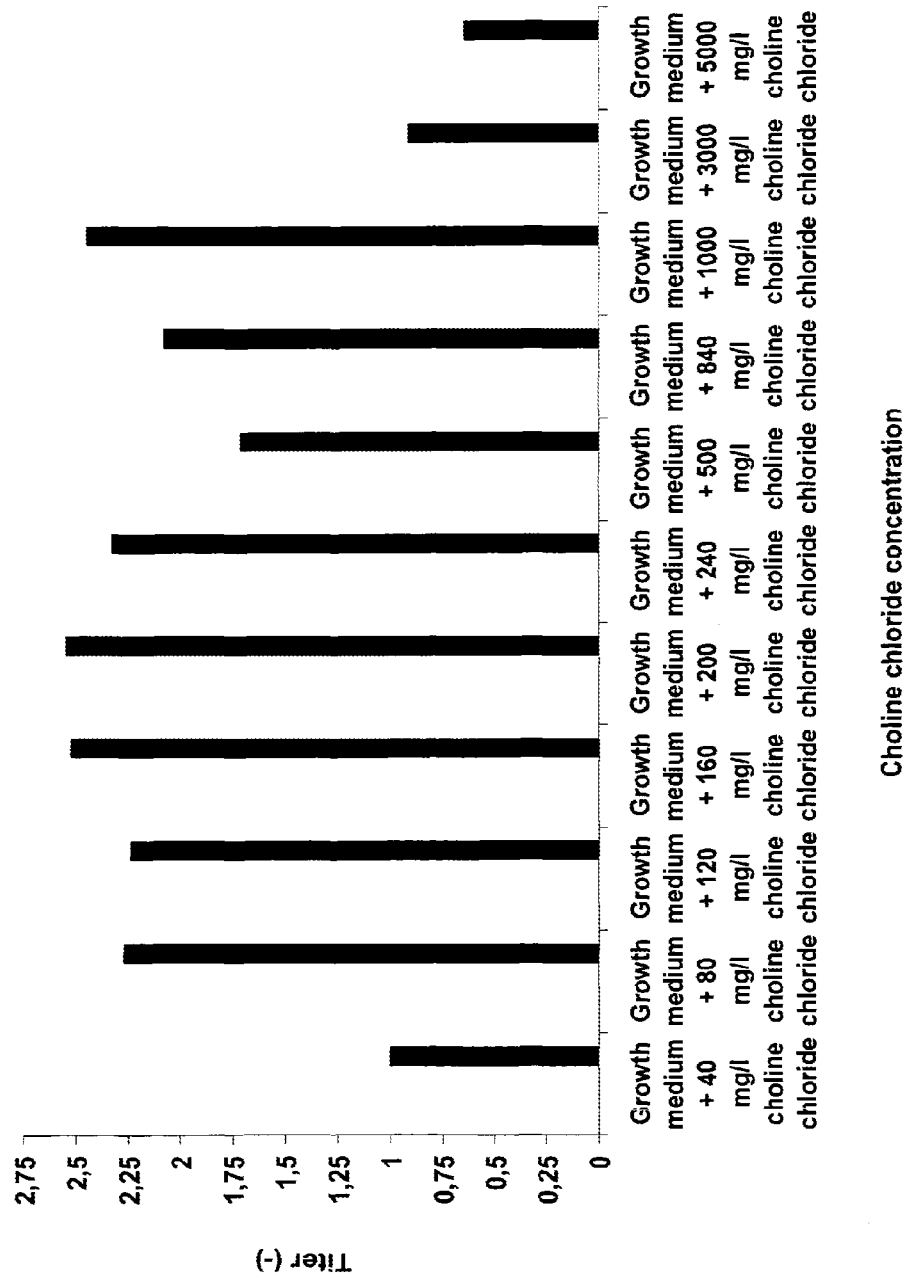
FIG. 14 depicts the normalized mAb3 antibody titer obtained after 13 days of cell culture using low choline growth medium supplemented with varying concentrations of choline chloride.
Figure 15:
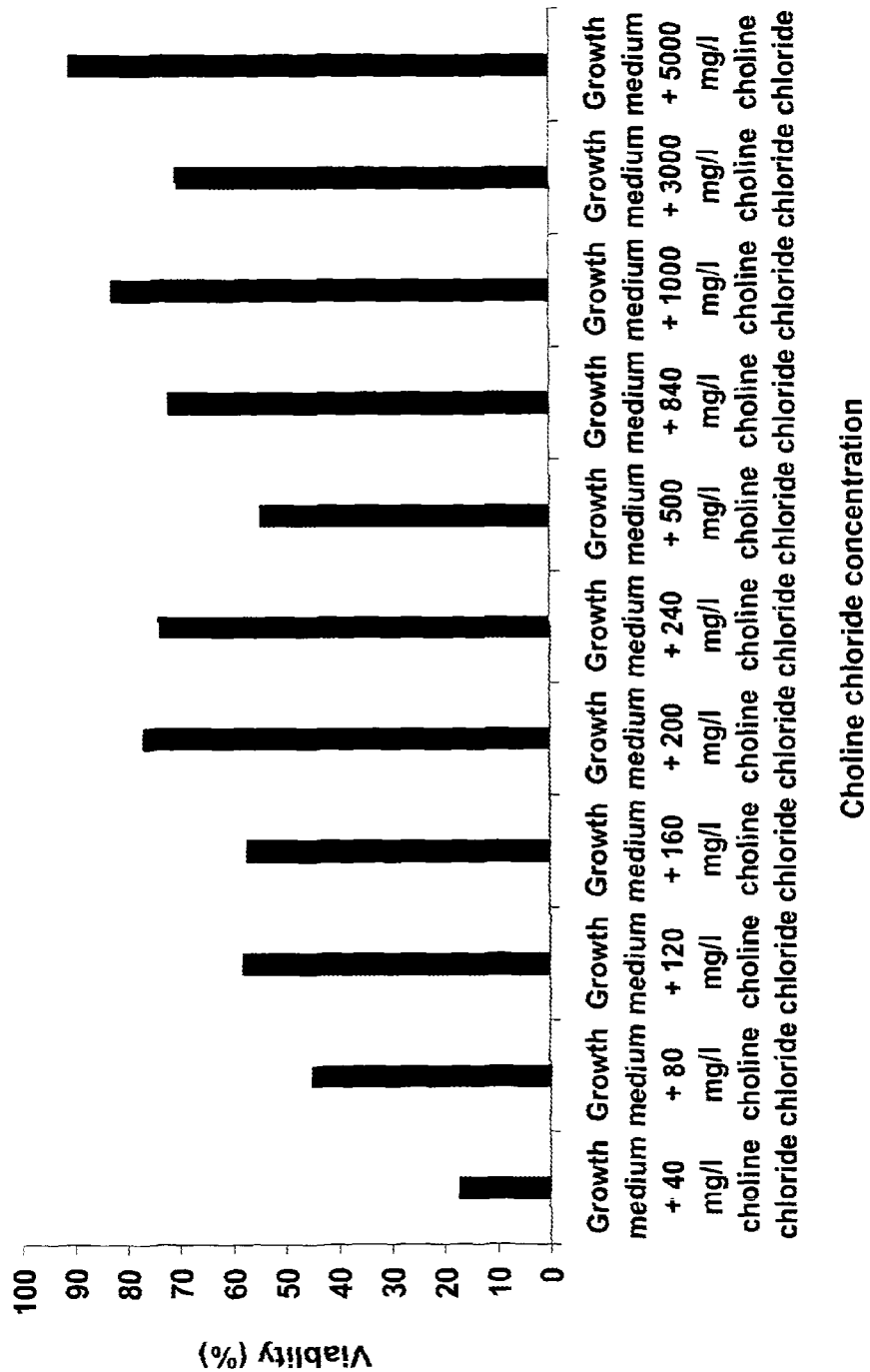
FIG. 15 depicts the viabilities of cells expressing mAb3 at day 13 of cell culture using low choline growth medium supplemented with varying concentrations of choline chloride.
Figure 16:
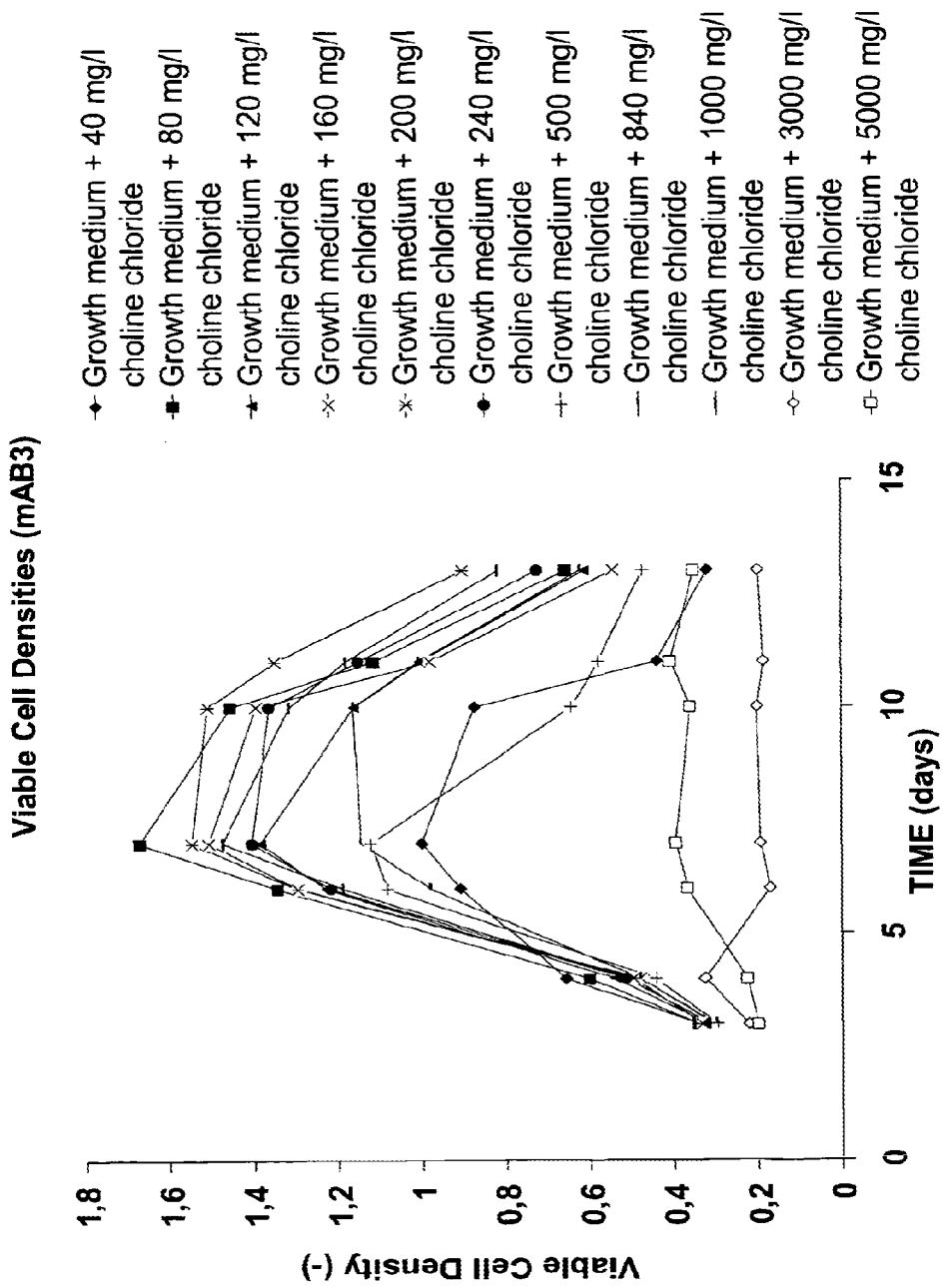
FIG. 16 depicts normalized viable cell densities of cells expressing mAb3 starting from day 3 (100%) to day 13 using low choline growth medium supplemented with varying concentrations of choline chloride.
Figure 17:
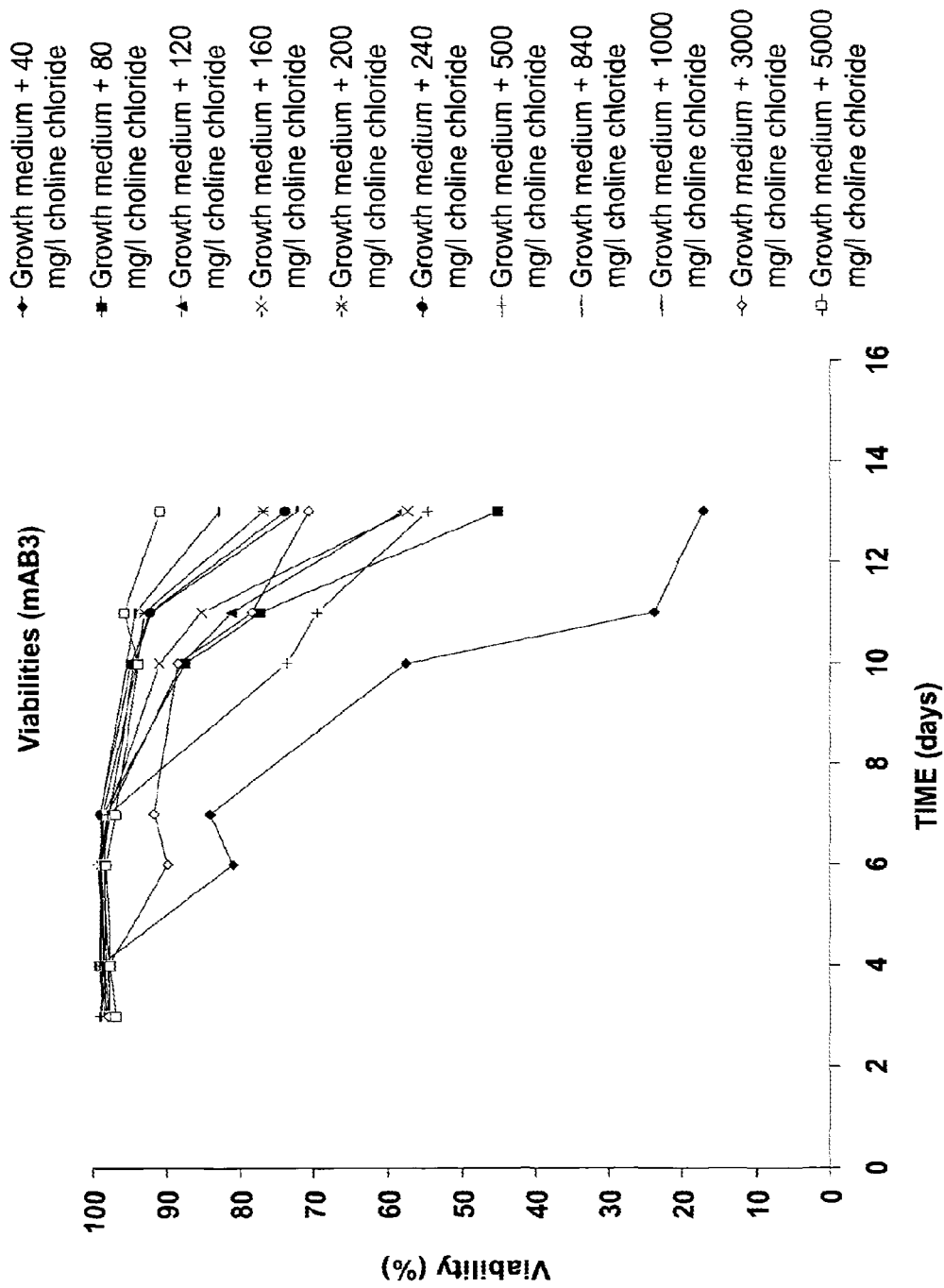
FIG. 17 depicts viabilities of cells expressing mAb3 starting from day 3 to day 13 using low choline growth medium supplemented with varying concentrations of choline chloride.
Figure 18:
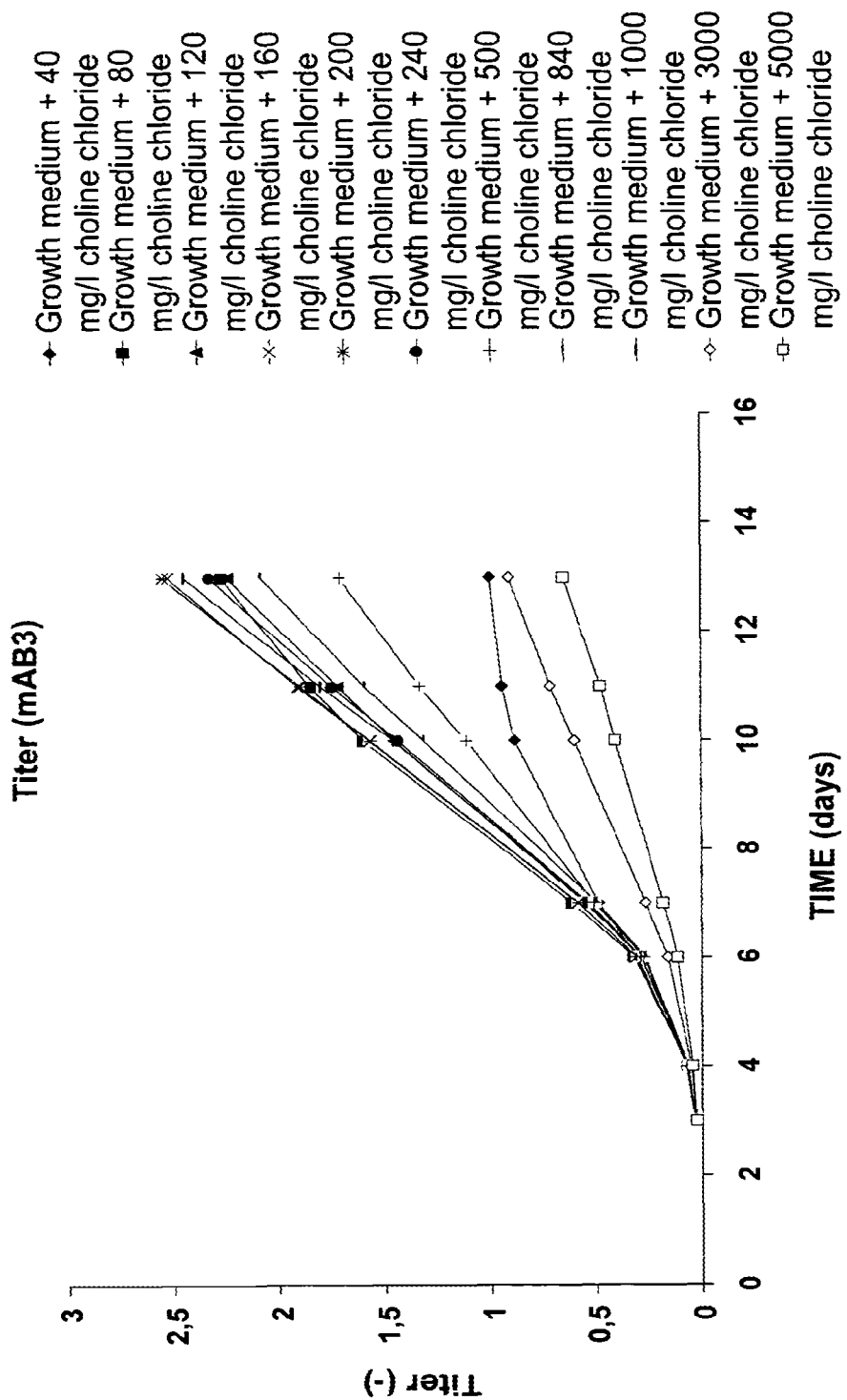
FIG. 18 depicts the normalized development of mAb3 antibody titer starting from day 3 to day 13 of cultivation using low choline growth medium supplemented with varying concentrations of choline chloride.
Figure 19:
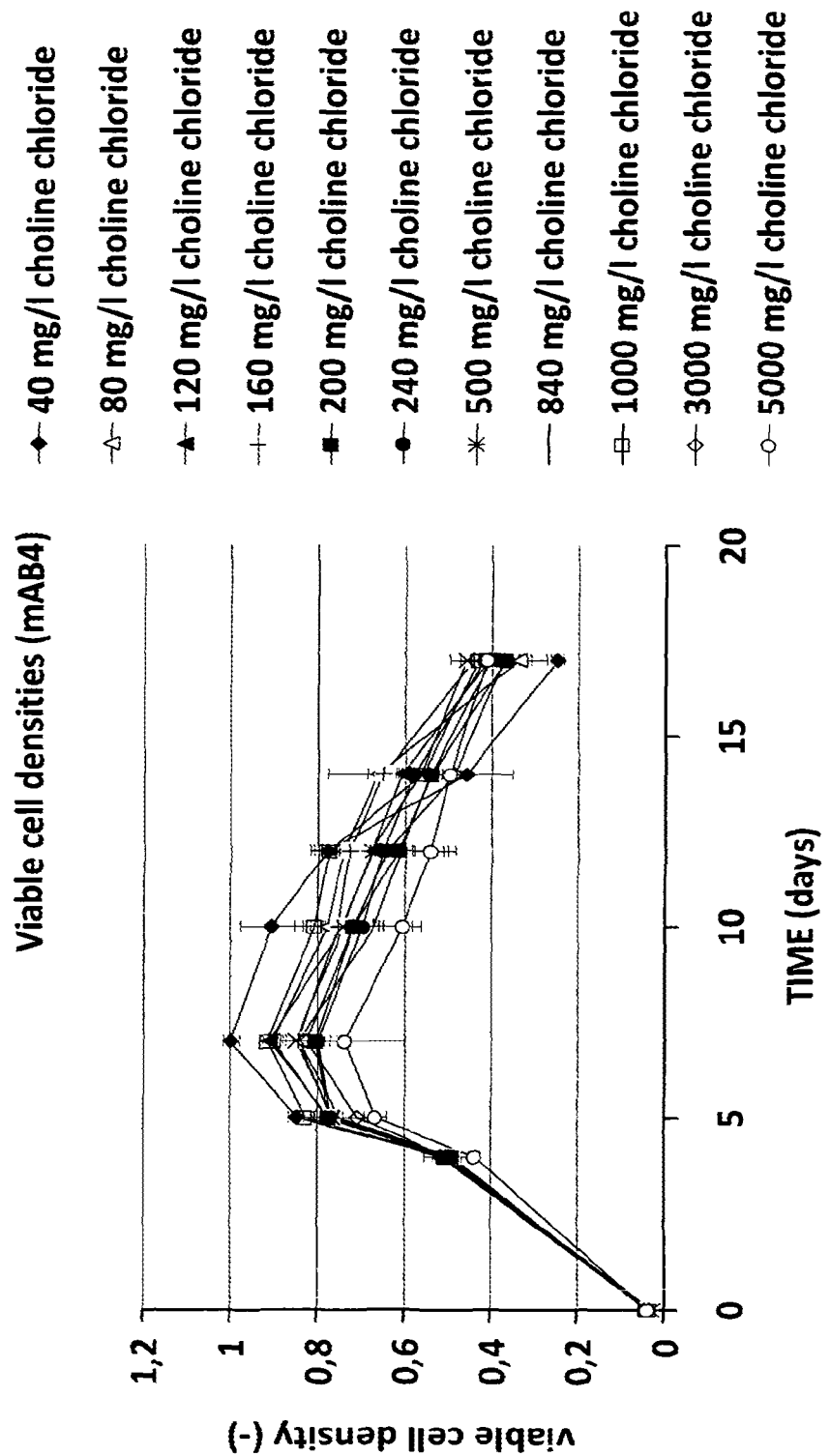
FIG. 19 depicts normalized viable cell densities of cells expressing mAb4 starting from day 0 to day 17 using low choline growth medium supplemented with varying concentrations of choline chloride.
Figure 20:
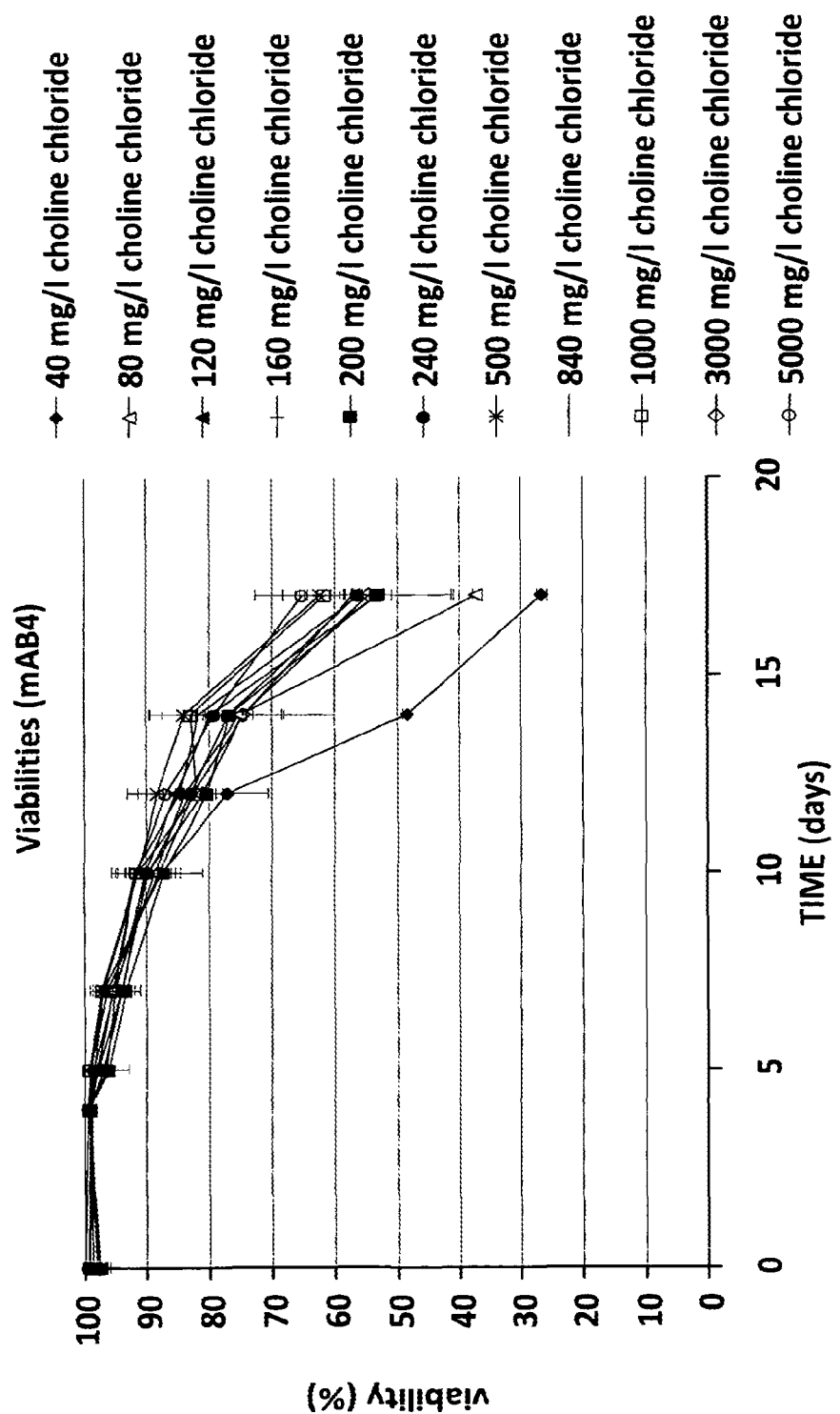
FIG. 20 depicts viabilities of cells expressing mAb4 starting from day 0 to day 17 using low choline growth medium supplemented with varying concentrations of choline chloride.
Figure 21:
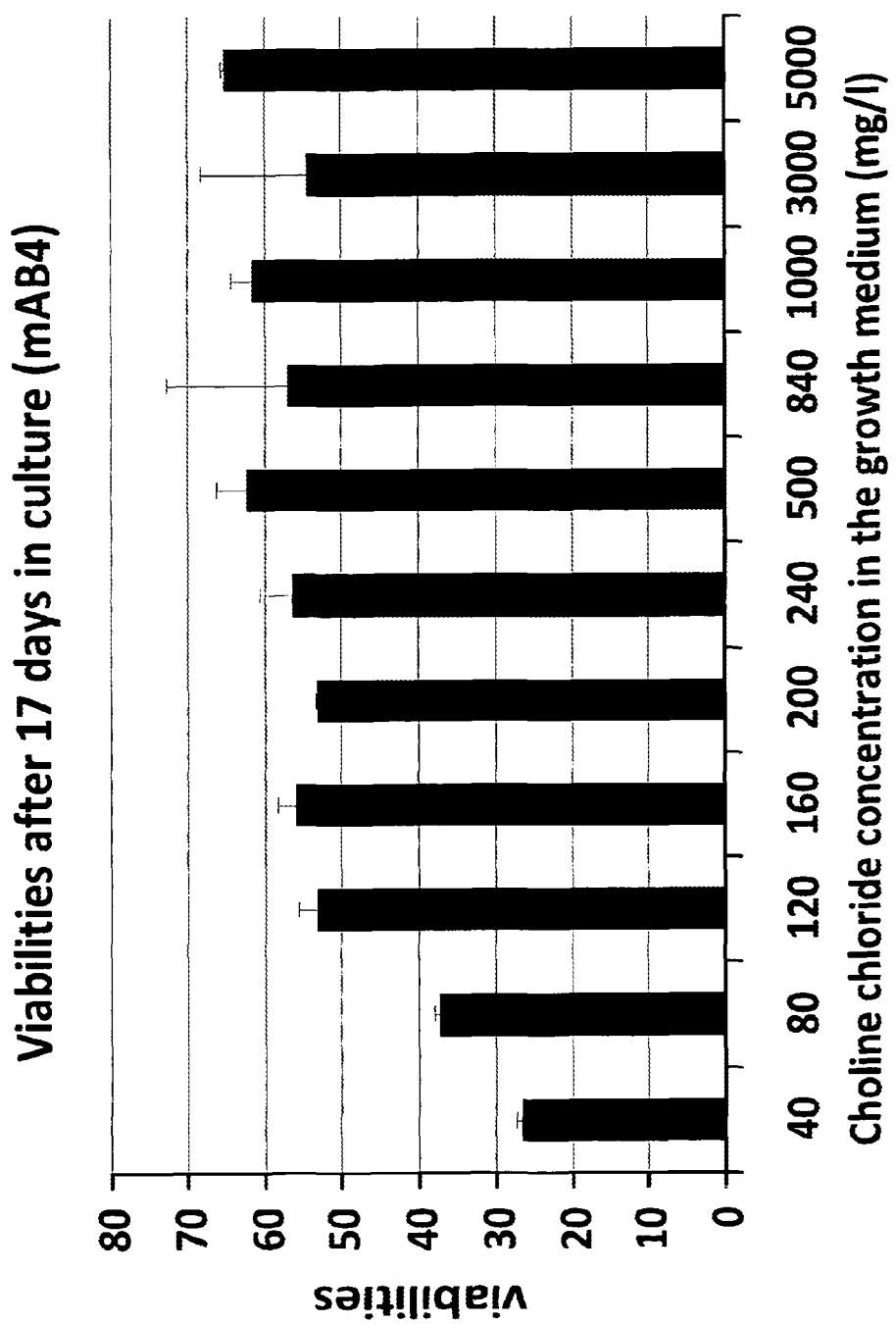
FIG. 21 depicts viabilities of cells expressing mAb4 at day 17 using low choline growth medium supplemented with varying concentrations of choline chloride.
Figure 22:
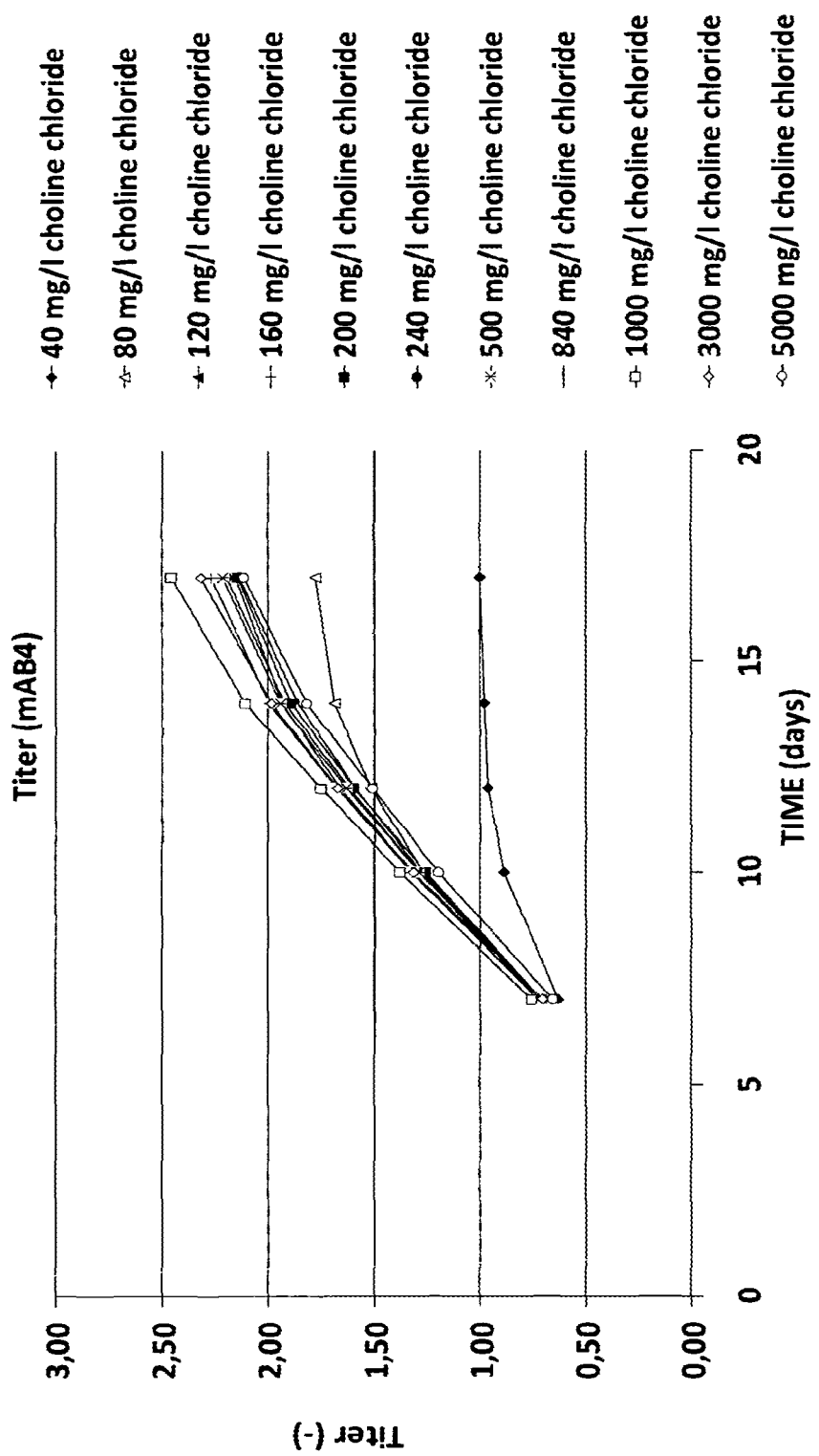
FIG. 22 depicts the normalized mAb4 antibody titer starting from day 7 to day 17 using low choline growth medium supplemented with varying concentrations of choline chloride.
Figure 23:
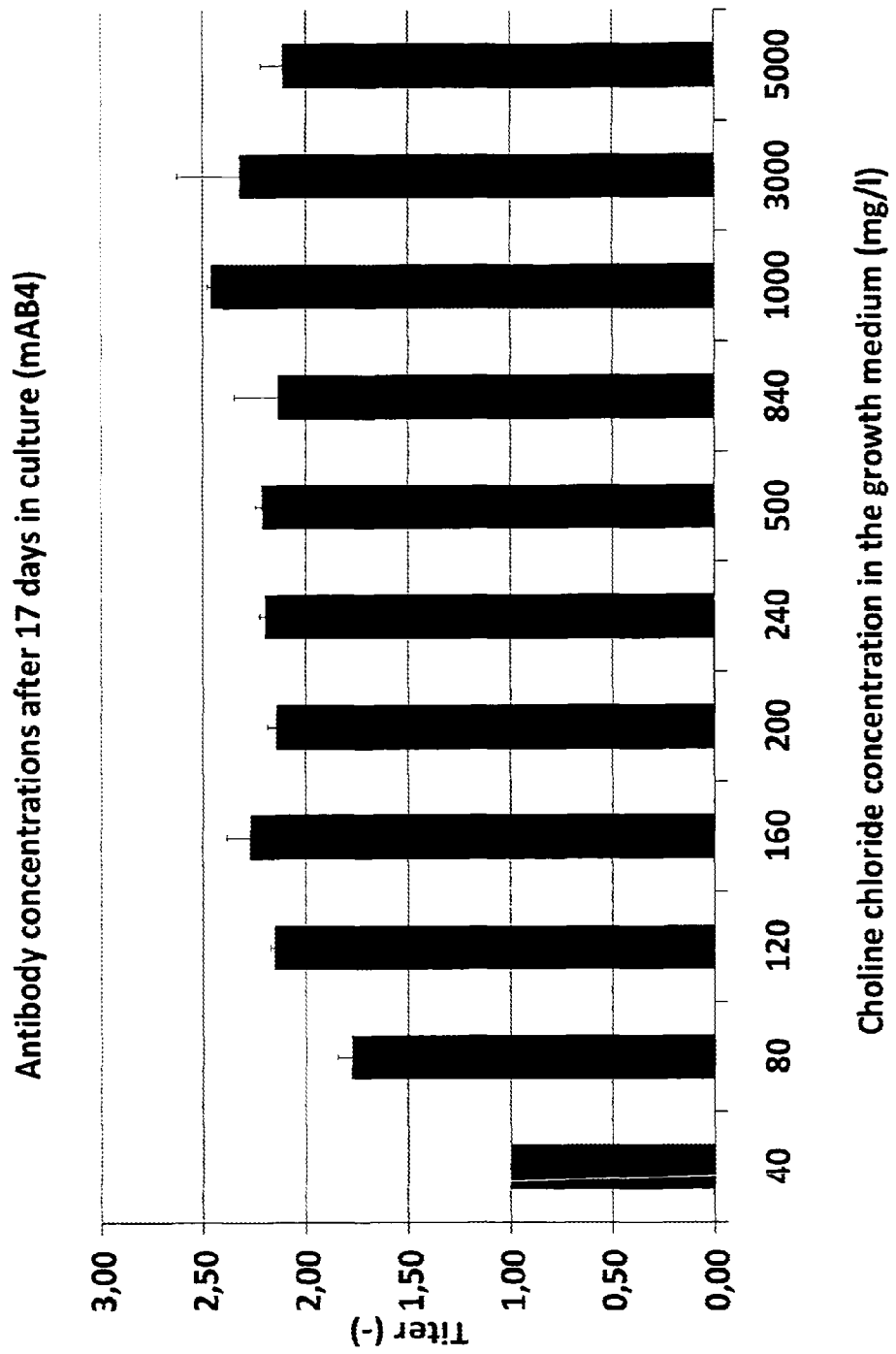
FIG. 23 depicts the normalized mAb4 antibody concentration at day 17 using low choline growth medium supplemented with varying concentrations of choline chloride.
Figure 24:
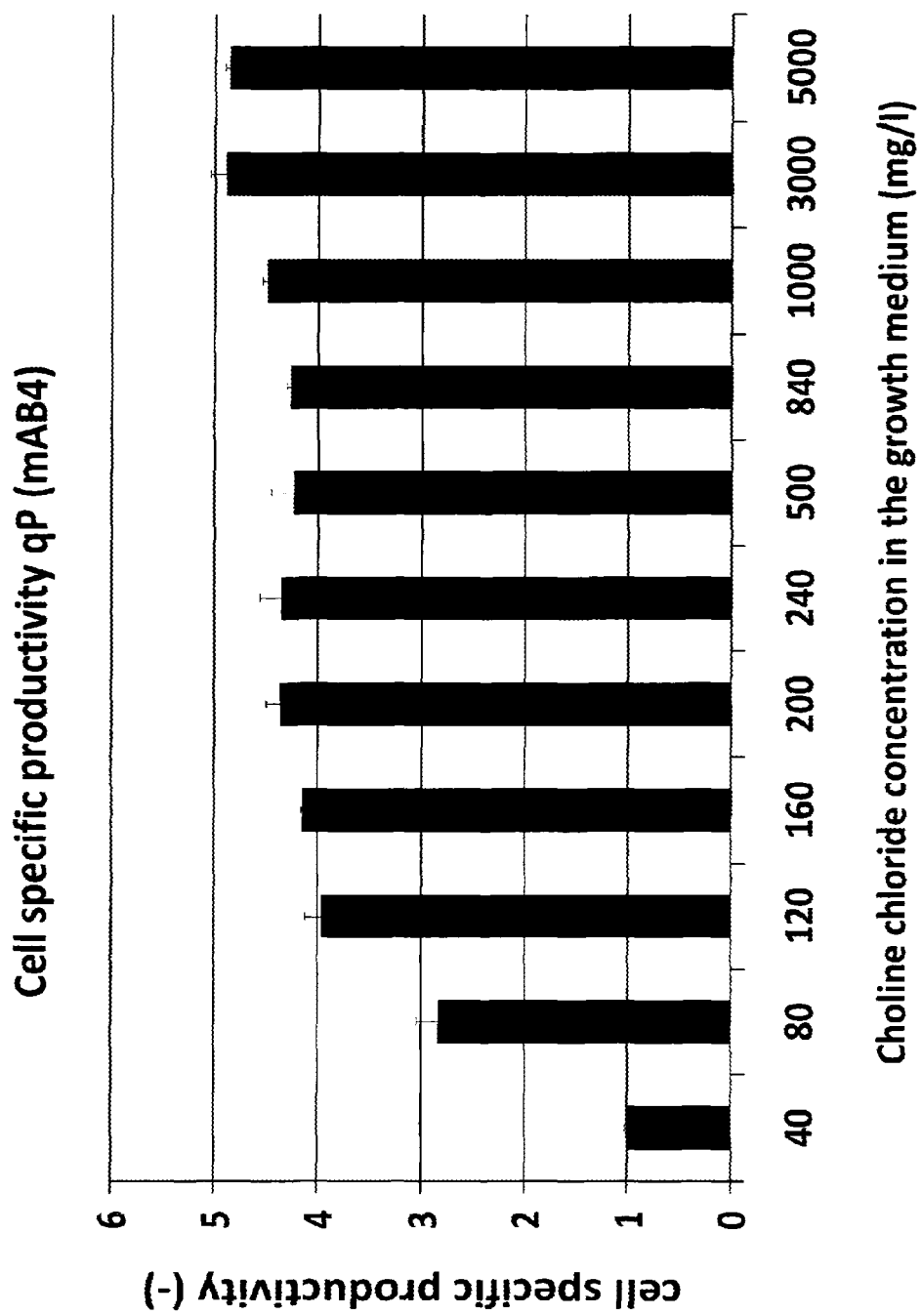
FIG. 24 depicts the normalized mean cell specific productivity (qP) of mAb4 expressing cells obtained within 17 days of cell culture using low choline chloride growth medium supplemented with varying concentrations of choline chloride.

FIG. 13 shows the results obtained for polypeptide titer in Experiment 4 carried out as fed-batch run in a bioreactor.

The polypeptide titer measured at day 11 for the inventive cell culture medium with high content of choline chloride is increased by 170% when compered with the comparative growth medium having only low amounts of choline chloride.

While the polypeptide titer obtained for inventive cell culture medium with high content of choline chloride is even superior to the polypeptide titer obtained by using for comparative purposes the production medium in the shake flask experiments, the experiment in the fed-batch run in the bioreactor reveals a slightly lower polypeptide titer in the inventive cell culture medium with high content of choline chloride when compared with the production medium. Nonetheless, the polypeptide titer obtained in the bioreactor by using the inventive cell culture medium with high content of choline chloride is very high and still at a comparable level with the polypeptide titer obtained by using for comparative purposes the production medium.

Experiment 4 in the bioreactor further confirms that the inventive cell culture medium with high content of choline chloride represents a suitable alternative to conventional production media by allowing achieving comparable polypeptide titers while the total amount of amino acids or the amounts of selected amino acids can be significantly reduced in the respective cell culture medium.

Experiment 4 in the bioreactor also proves one more time that the increase of the content of choline chloride in a typical growth medium helps to achieve a tremendous increase of polypeptide titer when using the growth medium for the production of polypeptides.

Addition of Different Concentrations of Choline Chloride to Growth Medium

In a further set of experiments, choline chloride is added in various concentrations (40; 80; 120; 160; 200; 240; 500; 840; 1000; 3000 and 5000 mg/l in total) to powder growth medium. The media thus obtained are used for producing mAb3 and mAb4, respectively, generally as outlined above.

Normalized antibody concentrations, normalized viable cell densities, and viabilities, for mAb3 and in addition for mAb4 the normalized cell specific productivity for the whole duration of the cultivation (13 resp. 17 days) are further depicted in FIG. 14 to FIG. 24.

As can be seen from these data, the lowest values in terms of viability and antibody concentration after 13 or 17 days in culture are achieved in growth medium with 40 mg/l of choline chloride in total. Concentrations of 3000 mg/l and more do not negatively affect the viability of the cells, but as the cells do not grow in those media, the antibody concentration stays below 1. Viabilities are higher for all choline concentrations higher than 40 mg/l. There seems to be a concentration depending effect of choline chloride on viability. Higher choline chloride concentrations in the medium resulted in a higher viability at the end of the cultivation.

The invention claimed is:

1. A fed-batch process for the production of a recombinant polypeptide comprising a production phase in which recombinant Chinese hamster ovary (CHO) cells are cultured and the recombinant polypeptide is expressed in a serum free and protein-free cell culture medium comprising at least 200 to at least 2500 mg/L of choline chloride or an equivalent amount of another choline salt and about 6.0 to about 10.0 mM glutamine.

2. The process according to claim 1 wherein the recombinant polypeptide is a recombinant antibody.

3. The process according to claim 1, wherein the cell culture medium comprises about 500 to about 2500 mg/L of choline chloride or an equivalent amount of another choline salt.

4. The process according to claim 3, wherein the cell culture medium comprises about 700 to about 2500 mg/L of choline chloride or an equivalent amount of another choline salt.

5. The process according to claim 4, wherein the cell culture medium comprises about 700 to about 1500 mg/L of choline chloride or an equivalent amount of another choline salt.

6. The process according to claim 1, wherein the cell culture medium has a total concentration of at least about 100 mmol/L amino acids.

7. The process according to claim 1, wherein the content of glutamine in the cell culture medium is in an amount of about 6.1 to about 8.2 mM.

* * * * *